(12) United States Patent
Ogg et al.

(10) Patent No.: US 12,116,633 B2
(45) Date of Patent: Oct. 15, 2024

(54) ANALYSIS OF T-CELL MONOTYPIA

(71) Applicant: Oxford University Innovation Limited, Oxford (GB)

(72) Inventors: Graham Ogg, Oxford (GB); Elizabeth Soilleux, Cambridge (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 15/515,745

(22) PCT Filed: Oct. 2, 2015

(86) PCT No.: PCT/GB2015/052896
§ 371 (c)(1),
(2) Date: Mar. 30, 2017

(87) PCT Pub. No.: WO2016/051205
PCT Pub. Date: Apr. 7, 2016

(65) Prior Publication Data
US 2017/0298445 A1 Oct. 19, 2017

(30) Foreign Application Priority Data

Oct. 3, 2014 (GB) ..................... 1417498
Jun. 12, 2015 (GB) ..................... 1510237

(51) Int. Cl.
| | |
|---|---|
| *C12Q 1/6886* | (2018.01) |
| *C07K 14/725* | (2006.01) |
| *C07K 16/28* | (2006.01) |
| *C12Q 1/6881* | (2018.01) |
| *G01N 33/574* | (2006.01) |

(52) U.S. Cl.
CPC ........ *C12Q 1/6886* (2013.01); *C07K 14/7051* (2013.01); *C07K 16/2803* (2013.01); *C12Q 1/6881* (2013.01); *G01N 33/57492* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2011/0086796 A1* | 4/2011 | Wang ............... | C12Q 1/6883 514/1.5 |
| 2012/0027739 A1 | 2/2012 | Jakobsen et al. | |
| 2013/0190194 A1* | 7/2013 | Tang ................ | G16B 20/20 506/9 |
| 2014/0255941 A1* | 9/2014 | Sugiyama .......... | C07K 14/7051 435/6.12 |
| 2014/0349402 A1* | 11/2014 | Cooper ............. | A61K 39/0011 435/455 |
| 2017/0066827 A1* | 3/2017 | Pulé ................ | A61P 43/00 |

FOREIGN PATENT DOCUMENTS

| | | |
|---|---|---|
| DE | 10109854 A1 | 9/2002 |
| EP | 2272977 A1 | 1/2011 |
| WO | 2006071088 A1 | 7/2006 |
| WO | 2014042226 A1 | 3/2014 |
| WO | 2015132598 A1 | 9/2015 |

OTHER PUBLICATIONS

Mineccia (Developmental and Comparative Immunology 2012 vol. 37 p. 279) (Year: 2012).*
Freeman et al. (Genome Research 2009 vol. 19 p. 1817). (Year: 2009).*
van Dongen et al., "Design and Standardization of PCR primers and protocols for detection of clonal immunoglobulin and T-cell receptor gene recombinations in suspect lymphoproliferations: Reprot of the BIOMED-2 Concerted Action BMH4-CT98-3936," Leukemia (2003):17:2257-2317.
Droese et al., "Validation of BIOMED-2 multiplex PCR tubes for detection of TCRB gene rearrangements in T-cell malignancies," Leukemia (2004); 18:1531-1538.
Braissant et al., "A Simpliefied In Situ Hybridization Protocol Using Non-radioactively Labeled Probes to Detect Abundant and Rare mRNAs on Tissue Sections," Biochemica (Jan. 1, 1998); pp. 10-16.
"A Guide to Nucleic Acid Labeling and Detection Systems," (Jan. 1, 2007) retrieved from the internet: URL: https://www.vectorlabs.com/data/brochures/MBB.pdf (36 pages).
"TCR C beta 1 (JOVI.1): sc-53196," (Jan. 1, 2012); retrieded from the inernet: URL:http://datasheets.scbt.com/sc-53196.pdf (1 page).
Tunnacliffe et al., "Sequence and evolution of the human T-cell antigen receptor beta-chain genes," Proc. Natl. Acad. Sci. (Aug. 1985); 82:5068-5072).
MacLean et al., "Identification of a predominant sequence variant of the T-cell receptor TCRBC1 gene," Immunogenetics (1997); 45:223-225.

(Continued)

*Primary Examiner* — Katherine D Salmon
(74) *Attorney, Agent, or Firm* — Baker, Donelson, Bearman, Caldwell & Berkowitz, P.C.

(57) ABSTRACT

A method of investigating the monotypia of a population of T-cells comprising detecting expression of the T cell receptor beta chain constant region TRBC1 and TRBC2, and/or the T cell receptor gamma chain constant region TRGC1 and TRGC, in a population of T-cells.

Figure 3:
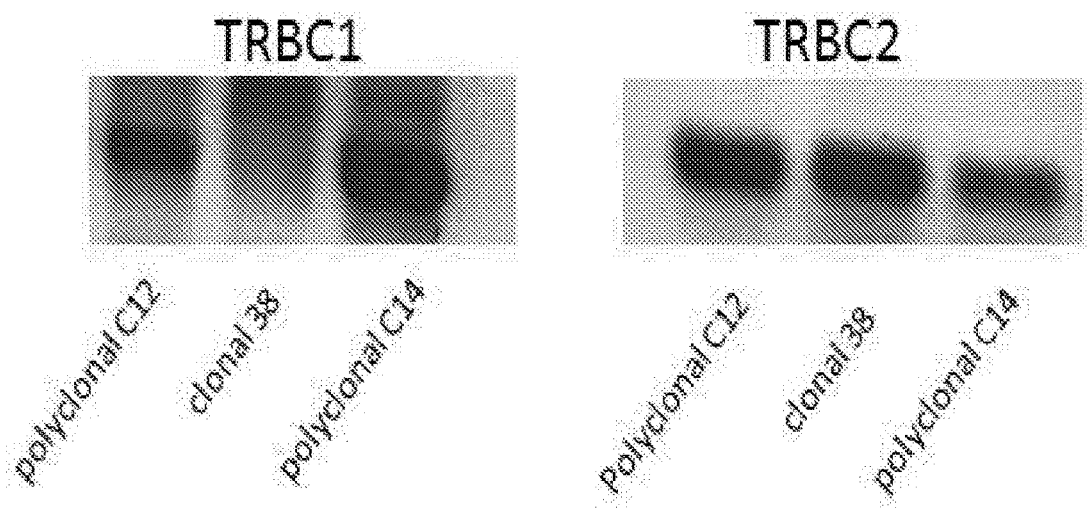

3 Claims, 13 Drawing Sheets
Specification includes a Sequence Listing.

(56) References Cited

OTHER PUBLICATIONS

Kempf et al., "EORTC, ISCL, and USCLC consensus recommendations for the treatment of primary cutaneous CD30-positive lymphoproliferative disorders: lymphomatoid papulosis and primary cutaneous anaplastic large-cell lymphoma," Blood (2011): 118(15): 4024-4035.

Roan et al., "CD4+ group 1 innate lymphoid cells form a functionally distinct ILC subset that is increased in systemic sclerosis," J. Immunol. (2016): 196(5): 2051-2062.

Buresi, et al: "Exon Duplication and Triplication in the Human T-Cell Receptor Gamma Constant Rgion Genes and RFLP in French, Lebanese, Tunisian, and Black African Populations", Innunogenetics, 29: 161-172, 1989.

\* cited by examiner

TRBC1 (SEQ ID NO: 1)

GTCAAGAGAAAGGATTTCTGAAGGCAGCCCTGGAAGTGGAGTTAGGAGCTTCTAACCCGTCATGGTTTCAATACACATTCTTCTTTTGCCAGCGCTTCTGAAGAGCTG*CTCTCACCTCTCTGCATCCC*AATAGATATCCCCCTATGTGCATGCACACCTGCACACTCACGGCTGAAATCTCCCTAACCCAGGGGGACCTTAGCATGCCTAAGTGACTAAACC<u>AATAAA</u>

TRBC2 (SEQ ID NO: 2)

GTCAAGAGAAAGGATTCCAGAGGC<u>*TAGCTCCAAAACCATCCCAG*</u>GTCATTCTTCATCCTCACCCAGGATTCTCCTGTACCTGCTCCCAATCTGTGTTCCTAAAAGTGATTCTCACTCTGCTTCTCATCTCCTACTTACATGAATACTTCTCTCTTTTTTCTGTTTCCCTGAAGATTGAGCTCCCAACCCCCAAGTACGAAATAGGCTAAACC<u>AATAAA</u>

Figure 1

TRBC1 Cβ1 primer (Forward: *ACCCTGTATGCTGTGCTGGT* (SEQ ID NO: 9), Reverse: *GGGATGCAGAGAGGTGAGAG* (SEQ ID NO: 10))

TRBC2 Cβ2 primer (Forward: *ACCTTGTATGCCGTGCTGGT* (SEQ ID NO: 11), Reverse: *CTGGGATGGTTTTGGAGCTA* (SEQ ID NO: 12))

Figure 2

TRGC1 protein - SEQ ID NO: 7

XKQLDADVSPKPTIFLPSIAETKLQKAGTYLCLLEKFFPDVIKIHWQEKKSNTILGSQEG
NTMKTNDTYMKFSWLTVPEKSLDKEHRCIVRHENNKNGVDQEIIFPPIKTDVITMDPKDN
CSKDANDTLLLQLTNTSAYYMYLLLLLKSVVYFAIITCCLLRRTAFCCNGEKS

TRGC2 protein - SEQ ID NO: 8

XKQLDADVSPKPTIFLPSIAETKLQKAGTYLCLLEKFFPDIIKIHWQEKKSNTILGSQEG
NTMKTNDTYMKFSWLTVPEESLDKEHRCIVRHENNKNGIDQEIIFPPIKT<u>DVTTVDPKYN
YSKDAN</u>DVITMDPKDNWSKDANDTLLLQLTNTSAYYTYLLLLLKSVVYFAIITCCLLRRT
AFCCNGEKS

Figure 5

TRBC1 protein sequence SEQ ID NO 5

DLNKVFPPEVAVFEPSEAEISHTQKATLVCLATGFFPDHVELSWWVNGKEVHSGVSTDPQPLKEQPALNDSRYCL
SSRLRVSATFWQNPRNHFRCQVQFYGLSENDEWTQDRAKPVTQIVSAEAWGRADCGFTSVSYQQGVLSATILYEI
LLGKATLYAVLVSALVLMAMVKRKDF

TRBC2 protein sequence SEQ ID NO 6

DLKNVFPPEVAVFEPSEAEISHTQKATLVCLATGFYPDHVELSWWVNGKEVHSGVSTDPQPLKEQPALNDSRYCL
SSRLRVSATFWQNPRNHFRCQVQFYGLSENDEWTQDRAKPVTQIVSAEAWGRADCGFTSESYQQGVLSATILYEI
LLGKATLYAVLVSALVLMAMVKRKDSRG

Figure 6

TRBC1*01
Exons and 3'UTR (SEQ ID NO: 3)

Aggacctgaacaaggtgttcccacccgaggtcgctgtgtttgagccatcagaagcagagatctcccacacccaaa
aggccacactggtgtgcctggccacaggcttcttccccgaccacgtggagctgagctggtgggtgaatgggaagg
aggtgcacagtggggtcagcacggacccgcagcccctcaaggagcagcccgccctcaatgactccagatactgcc
tgagcagccgcctgagggtctcggccaccttctggcagaaccccgcaaccacttccgctgtcaagtccagttct
acgggctctcggagaatgacgagtggacccaggatagggccaaacccgtcacccagatcgtcagcgccgaggcct
ggggtagagcagactgtggctttacctcggtgtcctaccagcaaggggtcctgtctgccaccatcctctatgaga
tcctgctagggaaggcc<u>accctgtatgctgtgctggt</u>cagcgcccttgtgttgatggccatggtcaagagaaagg
attt<u>c*tga*aggcagccctggaagtggagttaggagcttctaaccgtcatggtttcaatacac
attcttcttttgccagcgcttctgaagagctg<u>ctctcacctctctgcatcccaatagatatc
ccctatgtgcatgcacacctgcacactcacggctgaaatctccctaacccaggggaccttt
agcatgcctaagtga</u>ctaaacc*aataaa*aatgttctggtctggcctgactctgacttgtgaatgtctggata
gctccttggctgtctctgaactccctgtgactctccccattcagtcaggatagaaacaagaggtattcaaggaaa
atgcagactcttcacgtaagagggatgaggggcccaccttgagatcaatagcagaa tga stop codon
aataaa polyadenylation signal TRBC2*01
Exons and 3'UTR (SEQ ID NO: 4)

aggacctgaaaaacgtgttcccacccgaggtcgctgtgtttgagccatcagaagcagagatctcccacacccaaa
aggccacactggtgtgcctggccacaggcttctaccccgaccacgtggagctgagctggtgggtgaatgggaagg
aggtgcacagtggggtcagcacagacccgcagcccctcaaggagcagcccgccctcaatgactccagatactgcc
tgagcagccgcctgagggtctcggccaccttctggcagaaccccgcaaccacttccgctgtcaagtccagttct
acgggctctcggagaatgacgagtggacccaggatagggccaaacctgtcacccagatcgtcagcgccgaggcct
ggggtagagcagactgtggcttcacctccgagtcttaccagcaaggggtcctgtctgccaccatcctctatgaga
tcttgctagggaaggcc<u>accttgtatgccgtgctggt</u>cagtgccctcgtgctgatggccatggtcaagagaaagg
att<u>ccagaggc*tag*ctccaaaaccatccagg</u>tcattcttcatcctcacccaggattctcctg
tacctgctcccaatctgtgttcctaaaagtgattctcactctgcttctcatctcctacttac
atgaatacttctctcttttttctgtttccctgaagattgagctcccaaccccaagtacgaa
ataggctaaacc*aataaa*aaattgtgtgttgggcctggttgcatttcaggagtgtctgtggagttctgctcatc
actgacctatcttctgatttagggaaagcagcattcgcttggacatctgaagtgacagccctcttctctccacc
caatgctgctttctcctgttcatcctgatggaagtctcaacaca

*tag* stop codon at the start of the downstream primer

*aataaa* polyadenylation signal other underlined = primer binding sites

Figure 7

TRGC1*03

Exons and 3'UTR (SEQ ID NO: 13)

Gataaacaacttgatgcagatgtttcccccaagcccactattttttcttccttcaattgctgaaacaaagctccag
aaggctggaacatacctttgtcttcttgagaaattttcccctgatgttattaagatacattgggaagaaaagaag
agcaacacgattctgggatcccaggaggggaacaccatgaagactaatgacacatacatgaaatttagctggtta
acggtgccagaaaagtcactggacaaagaacacagatgtatcgtcagacatgagaataataaaaacggagttgat
caagaaattatctttcctccaataaagacagatgtcatcacaatggatcccaaagacaattgttcaaaagatgca
aatgatacactactgctgcagctcacaaacacctctgcatattacacgtacctcctcctgctcctcaagagtgtg
gtctattttgccatcatcacctgctgtctgcttagaagaacggctttctgctgcaatggagagaaatca<u>taa</u>cag
acggtggcacaaggaggccatcttttcctcatcggttattgtccctagaagcgtcttctgaggatctagttgggc
tttctttctgggtttgggccatttcagttcttatgtgtgtactattctatctattgtataacggttttcaaacca
gtgggcacacagagaacctcactctgtaataacaatgaggaatagccacggcgatctccagcaccaatctctcca
tgttttccacagctcctccagccaacccaaatagcgcctgctatagtgtagacatcctgcggcttctagccttgt
ccctctcttagtgttctttaatcagataactgcctggaagcctttcattttacacgccctgaagcagtcttcttt
gctagttgaattatgtggtgtgttttccgtaataagcaa<u>aataaa</u>tttaaaaaaatg taa stop codon
aataaa polyadenylation signal TRGC2*07
Exons and 3'UTR (SEQ ID NO: 14)

Gataaacaacttgatgcagatgtttcccccaagcccactattttttcttccttcaattgctgaaacaaaactccag
aaggctggaacatacctttgtcttcttgagaaattttcccagatattattaagatacattggcaagaaaagaag
agcaacacgattctgggatcccaggaggggaacaccatgaagactaacgacacatacatgaaatttagctggtta
acggtgccagaagagtcactggacaaagaacacagatgtatcgtcagacatgagaataataaaaacggaattgat
caagaaattatctttcctccaataaagaca**gatgtcaccacagtggatcccaaatacaattattcaa
aggatgcaaat**gatgtcatcacaatggatcccaaagacaattggtcaaaagatgcaaatgatacactactgct
gcagctcacaaacacctctgcatattacatgtacctcctcctgctcctcaagagtgtggtctattttgccatcat
cacctgctgtctgcttggaagaacggctttctgctgcaatggagagaaatca<u>taa</u>cagacggtggcacaaggagg
ccatcttttcctcatcggttattgtccctagaagcgtcttctgaggatctagttgggctttctttctgggtttgg
gccatttcagttctcatgtgtgtactattctatctattgtaatggttttcaaaccagtgggcacacagagaac
ctcactctgtaataacaatgaggaatagccatggcgatctccagcaccaatctctccatgttttccacagctcct
ccagccaacccaaatagcgcctgctatagtgtagacagcctgcggcttctagccttgtccctctcttagtgttct
taatcagataactgcctggaagcctttcattttacacgccctgaagcagtcttctttgctagttgaattatgtg
gtgtgttttccgtaataagcaa<u>aataaa</u>tttaaaaaaatgaaaagtt

<u>taa</u> stop codon

<u>aataaa</u> polyadenylation signal

Figure 8

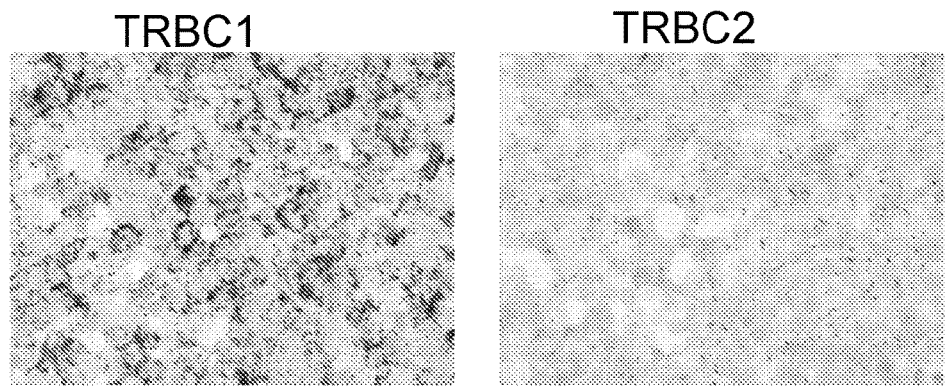
Figure 10
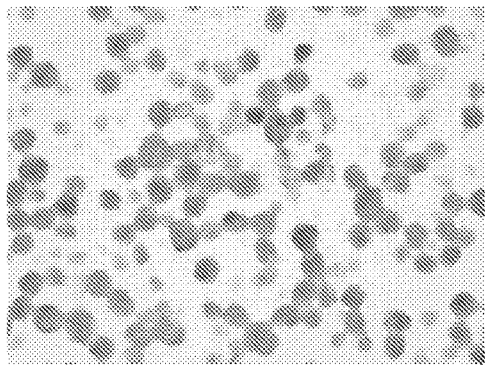 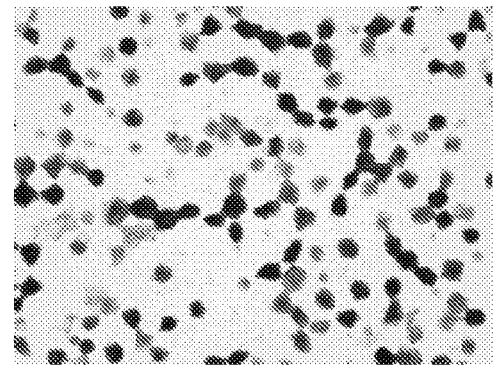
Figure 11

TRBC1 TRBC2
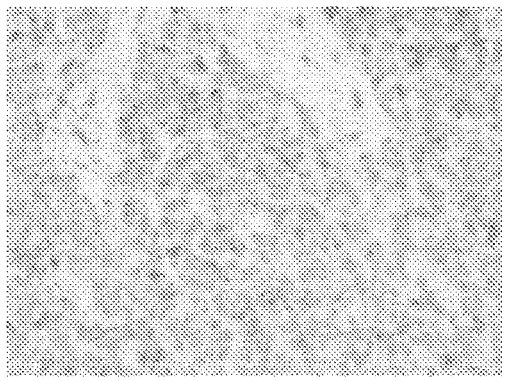
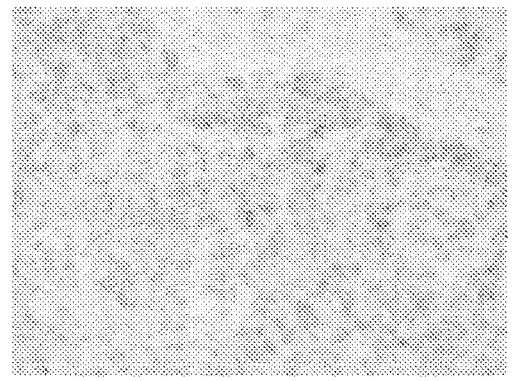
Figure 14
TRBC1 TRBC2
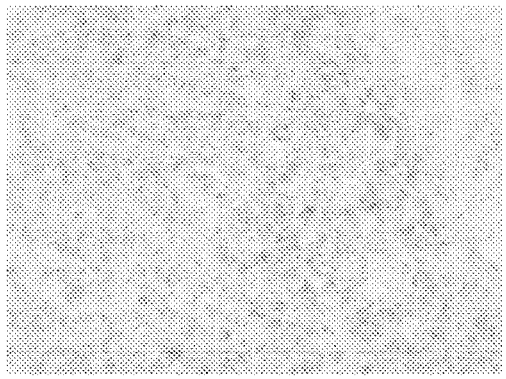
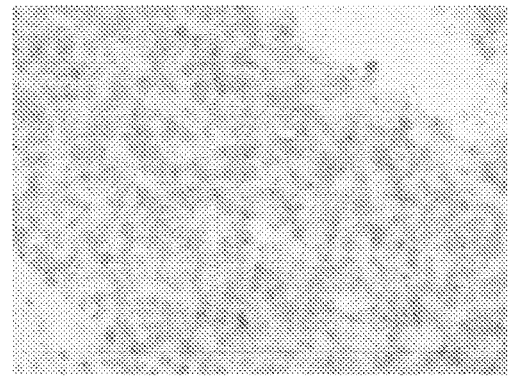
Figure 15

SEQ ID NO: 17 – ACCATGACGGGTTAGAAGCT

SEQ ID NO: 18 – TTAGGGAGATTTCAGCCGTGA

SEQ ID NO: 19 – TGGGTTAGGGAGATTTCAGCC

SEQ ID NO: 20 – ATTGGGATGCAGAGAGGTGAG

SEQ ID NO: 21 – TGTGTATTGAAACCATGACGG

SEQ ID NO: 22 – CTAACTCCACTTCCAGGGCTG

SEQ ID NO: 23 – TGTAAGTAGGAGATGAGAAGCA

SEQ ID NO: 24 – TTGGGAGCAGGTACAGGAGAAT

SEQ ID NO: 25 – AGGATGAAGAATGACCTGGGAT

SEQ ID NO: 26 – GCCTATTTCGTACTTGGGGGT

SEQ ID NO: 27 – GTAAGTAGGAGATGAGAAGCAG

SEQ ID NO: 28 – AGGAACACAGATTGGGAGCAG

SEQ ID NO: 29 – CCTGGGATGGTTTTGGAGCTA

Figure 16

TTTATTGGTTTAGCCTATTTCGTACTTGGGGGTTGGGAGCTCAATCTTCAGGGAAACAGAAAAAAGAG
AGAAGTATTCATGTAAGTAGGAGATGAGAAGCAGAGTGAGAATCACTTTTAGGAACACAGATTGGGA
GCAGGTACAGGAGAATCCTGGGTGAGGATGAAGAATGANNNNNNNNNNNNNNNNNNNNGCCTCTGGA
ATCCTTTCTCTTGAC (SEQ ID NO: 32)

| Oligo | Sequence | Length | Start | Stop | TM (Eurofins Tm) | GC % | Eurofins Operon Primer Dimer | Self complem-entarity | Self 3' complem-entarity |
|---|---|---|---|---|---|---|---|---|---|
| T2.1 (2PBF 4) | GCCTATTTCGTACTTGGGGGT | 21 | 13 | 33 | 59.79 (62.6) | 52.38 | 4 | 4.0 | 0.0 |
| T2.2 (ES2) | GTAAGTAGGAGATGAGAAGCAG | 22 | 81 | 102 | 60.8 | 45.45 | 0 | - | - |
| T2.3 (2PBR 2) | AGGAACACAGATTGGGAGCAG | 21 | 119 | 139 | 62.57 | 52.38 | 0 | 2.0 | 0.0 |
| T2.4 (2PBF 4) | NNNNNNNNNNNNNNNNNNNNN | 21 | 174 | 194 | 62.57 | 52.38 | 4 | 4.0 | 3.0 |

Figure 17

TTTATTGGTTTAGTCACTTAGGCATGCTAAGGTCCCCCTGGGTTAGGGAGATTTCAGCCGTGAGTGTG
CAGGTGTGCATGCACATAGGGGGATATCTATTGGGATGCAGAGAGGTGAGAGCAGCTCTTCAGAAGCG
CTGGCAAAAGAAGAATGTGTATTGAAACCATGACGGGTTAGAAGCTCTAACTCACTTCAGGCTG
CCTTCAGAAATCCTTTCTCTTGAC (SEQ ID NO: 33)

| Oligo | Sequence | Length | Start | Stop | TM (Eurofins Tm) | GC % | Eurofins Operon Priner Dimer | Self complem-entarity | Self 3' complem-entarity |
|---|---|---|---|---|---|---|---|---|---|
| T1.1 (PB8 F) | TGGGTTAGGGAGATTTC AGCC | 21 | 39 | 59 | 59.44 (62.6) | 52.38 | 0 | 4.0 | 2.0 |
| T1.2 (PB7 F) | ATTGGGATGCAGAGAGG TGAG | 21 | 98 | 118 | 59.51 (62.6) | 52.38 | 4 | 4.0 | 0.0 |
| T1.3 (ES1) * | TGTGTATTGAAACCATG ACGG | 21 | 152 | 171 | (58.7) | 42.9 | 4 | - | - |
| T1.4 (PB2 R) | | 21 | 184 | 204 | 60.07 (64.5) | 57.14 | 0 | 4.0 | 0.0 |

Figure 18

ANALYSIS OF T-CELL MONOTYPIA

CROSS-REFERENCE TO RELATED APPLICATIONS

This application is a U.S. National Phase of International Application No. PCT/GB2015/052896, filed Oct. 2, 2015, which claims priority to GB Application No. 1510237.9, filed Jun. 12, 2015 and GB Application No. 1417498.1, filed Oct. 3, 2014, the disclosures of which are incorporated herein by reference.

This invention relates to methods for investigating T-cell monotypia, and in particular to primers, probes and other specific detection reagents including oligonucleotides and antibodies, that are capable of distinguishing inflammatory (also known as reactive or benign) T-cell infiltrates from neoplastic (also known as malignant or lymphomatous) T-cell infiltrates. The present invention also relates to methods of distinguishing inflammatory T-cell infiltrates from neoplastic T-cell infiltrates.

Analysis of the monotypia of tissue infiltrating lymphocytes is an important and common clinico-pathological question in order to differentiate inflammatory infiltrates from neoplastic infiltrates (eg lymphoma or leukaemia). In the setting of B cell lymphoma, this is frequently undertaken at an early stage of investigation by using detection reagents that are specific for kappa and lambda light chains. A skewed kappa:lambda ratio raises the possibility that a tissue B cell infiltrate is neoplastic rather than reactive/inflammatory. When all of the B-cells in a B cell population only express one light chain (only kappa or only lambda), it is known as a monotypic population. The presence of a monotypic population supports the possibility that there is a clonal or neoplastic B cell population present, and so is a commonly used diagnostic investigation in clinical practice. A monoclonal population of B-cells would all have identical V-regions; this can only be determined by determining the exact sequence of the V-region or some surrogate of the sequence, eg PCR fragment size using specific primers.

However in the setting of T cell infiltrates, the designation of monotypia has not been possible because kappa and lambda chains are not expressed by T cells. Instead the diagnosis of a T cell neoplasm is supported by undertaking T cell receptor gene rearrangement studies where the rearranged T cell receptor genes are amplified by PCR and then characterised by gel or genescanner analysis to examine the presence of dominant clonally-amplified T cell receptor variable regions (alpha, beta, gamma or delta). This is an expensive and time-consuming approach compared to kappa/lambda staining, and is only performed at specialist centres. Furthermore it is still often difficult to distinguish reactive from neoplastic infiltrates using T cell receptor gene rearrangement studies, as the reactive infiltrates are also frequently associated with oligoclonal antigen-specific T cell expansions and the neoplastic populations can have an associated anti-tumour or other inflammatory T cell response. Interpretation of the data is therefore highly specialised and open to debate. In practice, T cell receptor gene rearrangement studies are interpreted in the context of the clinical background and associated histological features, but interpretation is hampered by the inability to visualise histologically the T-cells contributing to the mono-/oligo- or polyclonality, unlike for B-cells where kappa and lambda can be used. Therefore a simple test to distinguish inflammatory T cell populations from neoplastic T-cell populations would be of value in clinico-pathological practice and also as a research tool in human and non-human systems to examine the degree of monotypia of T cell populations, as a surrogate for T-cell clonality. Examples of applications of such a system would be the analysis of T cell monotypia in tissues of lymph nodes, skin, gut, bone marrow, lung, kidney, blood and indeed any other tissues. Additionally, determination of whether a T-cell population is monotypic as a surrogate for clonality might be important in predicting prognosis in a range of conditions other than T-cell lymphoma, where the effects of the T-cell population are important, for example (but not limited to), T-cell populations infiltrating other tumours, or T-cell populations causing pathology in various organs, such as in autoimmune disease or following transplantation of bone marrow or solid organs.

It is an aim of the present invention to provide methods and reagents that will enable the analysis of T cell monotypia and provide supporting evidence of clonality. This information may then be used to distinguish inflammatory cells from neoplastic cells and/or to comment on the likelihood a population is clonal in other circumstances where this may be predictive of outcome, drug response etc.

All T cells, including Natural Killer T cells (NKT cells), express multiple copies of a T cell receptor (TCR) on their surface. TCRs are composed of two chains (an alpha and beta chain or a gamma and a delta chain), each of which has a constant region and a variable region. The variable region, due to somatic (genetic) recombinations during T-cell development, can exist in many millions of different sequences. To be monoclonal a T-cell population must have T-cells in which all V-regions are identical. Each chain also has a constant region. All alpha constant regions are the same, however the beta constant regions may exist in two forms as TRBC1 (also known as TCRBC1) and TRBC2 (also known as TCRBC2). TRBC1 and TRBC2 are discussed in Droese et al. Leukemia (2004) 18, 1531-1538. Similarly, the gamma chain comprises one of two very similar constant regions referred to as TRGC1 (also known as TCRG1) and TRGC2 (also known as TCRG2). The overall structure of the T cell receptor determines its specificity for binding to antigen presented by MHC or MHC-like molecules. In a monotypic population, all (or substantially all) T-cells in a population will have the same constant region, for example all will be TCRBC1 or TCRBC2. In a polytypic population of T cells, some of the T cells have receptors with one form of each of these constant regions and some T cells have receptors with the other form of each of these constant regions, but each individual T-cell will only have one type of constant region.

In a first aspect, the present invention provides a method of investigating the monotypia of a population of T-cells (including NKT cells) comprising detecting expression of at least one variant of the T cell receptor beta and/or gamma chain constant region.

T cells may be defined as cells which express a T cell receptor at the RNA and/or protein level. A population of T cells may include all T cells in a specimen or all T cells with a particular morphology or all T cells defined by particular biomarker expression at protein/RNA/DNA/carbohydrate level. The T cells may be any type of T cells, for example helper T cells, cytotoxic T cells, memory T cells, regulatory T cells or natural killer T cells. A T cell population where all of the cells express one beta constant region or one gamma constant region may be defined as monotypic. A monoclonal population of T cells results from expansion of a single cell and therefore the T cells in the population have T cell receptors with identical constant regions and identical variable regions. A monotypic T cell population is a population of T cells that all express the same constant region variant, either TRBC1 or TRBC2 and either TRGC1 or TRGC2. A completely monotypic T cell population is also likely to be a monoclonal population but testing for monotypia of one or even both T cell receptor constant regions does not definitively prove monoclonality, although it is an excellent surrogate for it. Screening for monotypia is cheaper and easier than screening for monoclonality but provides that same or enhanced diagnostic, therapeutic and predictive options. A monotypic population is defined as a population where most of the T-cells in the population have the same TRBC type (i.e., all TRBC1 or TRBC2 depending on which TRBC gene segment is used; the same constant region), whereas monoclonality is defined as all the T-cells in the population having the same variable region sequence. There are many million variable region sequences, but only two possible TRBC types. It is much easier and cheaper to screen for two TRBC types than millions of variable regions.

The variant T cell receptor beta or gamma chain constant region that is specifically detected may be at least one beta and/or gamma chain constant region selected from TRBC1, TRBC2, TRGC1 and TRGC2. The method may comprise detecting one of TRBC1, TRBC2, TRGC1 and TRGC2. The method may comprise detecting two of TRBC1, TRBC2, TRGC1 and TRGC2. The method may comprise detecting three of TRBC1, TRBC2, TRGC1 and TRGC2. The method may comprise detecting all of TRBC1, TRBC2, TRGC1 and TRGC2.

The variant of the T cell receptor beta constant region that is specifically detected may be at least one of TRBC1 or TRBC2 or both. As described above TRBC1 and TRBC2 are a pair of alternative beta chain constant regions and a T cell will express either TRBC1 or TRBC2 but not both. Therefore in a population of T cells the percentage of cells that express TRBC1 or TRBC2 can be determined by detecting one or both of these variants.

The variant of the T cell receptor gamma constant region that is specifically detected may be at least one of TRGC1 and TRGC2 or both. As described above TRGC1 and TRGC2 are a pair of alternative gamma chain constant regions, and a T cell will express either TRGC1 or TRGC2 but not both. Therefore in a population of T cells the percentage of cells that express TRGC1 or TRGC2 can be determined by detecting one or both of these variants.

The method may comprise detecting one or both beta constant chain variant(s) and/or one or both gamma constant chain variant(s).

Preferably the method of the invention comprises detection of TRBC1 and TRBC2, and/or TRGC1 and TRGC2. Preferably the relative amount of TRBC1 to TRBC2, and/or TRGC1 to TRGC2 in a cell population is determined in the method of the invention. Preferably the method of the invention allows the determination of the number of cells, or the relative number of cells in a particular T-cell population that express a particular TCR constant region.

Any suitable method may be used for the detection of one of more of TRBC1, TRBC2, TRGC1 and/or TRGC2. The differences in the constant regions of these receptors may be detected at one or more of the DNA, RNA or protein level. The skilled person will appreciate that there are many ways differences in the T cell receptor constant regions can be detected and that the examples presented here are not intended to be exhaustive.

PCR may then be used to detect the relative amounts of one or more of TRBC1, TRBC2, TRGC1 and TRGC2. PCR may be performed on extracted DNA or RNA, or on whole T cells or tissue samples. The method may comprise use of a pair of oligonucleotides suitable for use in a PCR reaction to specifically detect TRBC1, TRBC2, TRGC1 or TRGC2.

The method may comprise simultaneous use of more than one pair of oligonucleotides suitable for use in PCR reactions to specifically detect more than one of TRBC1, TRBC2, TRGC1 or TRGC2. An advantage of using PCR to detect TRBC1, TRBC2, TRGC1 and/or TRGC2 DNA or RNA is that only a small sample of cells is required and there is no need to provide a suitable section of tissue. A further advantage of using PCR to detect TRBC1, TRBC2, TRGC1 and/or TRGC2 DNA or RNA is that it may be done on samples of non-solid tissues such as blood and bone marrow aspirates, as well as on DNA or RNA extracted from solid or non-solid tissue samples.

TRBC1, TRBC2, TRGC1 and/or TRGC2 DNA, RNA or protein may be detected in situ in T cells in a tissue sample, section or cell culture.

TRBC1, TRBC2, TRGC1 and/or TRGC2 DNA or RNA or protein may be detected in situ, for example in a tissue section, by in situ hybridisation and immunohistochemistry. Such methods may use antibodies which are able to distinguish between the different beta and gamma chain constant regions. Alternatively labelled DNA or RNA probes may be used which can distinguish between the different beta and gamma chain constant regions. The antibodies or DNA or RNA probes may be directly or indirectly labelled. A label used to facilitate detection of a molecule, such as an oligonucleotide or antibody may include any known label, including fluorescent, luminescent, light scattering and/or colorimetric labels. Suitable labels include enzymes, and fluorescent and chromogenic moieties, as well as radio-nucleotides, substrates, cofactors, inhibitors, magnetic particles and the like. If the label is an enzyme it may be horse radish peroxidase, alkaline phosphatase, beta-galactosidase, glucose oxidase and the like, as well as various proteases and phospholipases. Other labels include fluorohores or haptens such as digoxygenin or dinitrophenyl/dinitrophenol. Such labelled probes are commonly used in in situ hybridisation methods. The binding of antibodies or labelled DNA or RNA probes may be detected "by eye" or using digital pathology analytical techniques. Digital pathology analytical techniques may be used to assess tissue sample or sections labelled with one or more specific detection reagents, each of which specifically recognises one of the constant regions. For example, the digital pathology analytical techniques may count the number of cells that are labelled with a specific detection reagent and may calculate the percentage of T cells expressing a particular constant region. Digital pathology analytical techniques may also process an image, for example of a stained tissue section in order to assess the distribution of T cells labelled with a specific detection reagent that specifically recognises one of the T cell receptor constant regions. Digital pathology analysis may also decide whether or not individual cells should be regarded as positive for detection of a particular constant region, for example by counting numbers of dots associated with a cell, where dots represent positive staining or by analysing staining intensity. The skilled person will appreciate that, depending on the method used to detect the T cell constant region, different digital pathology analytical approaches will be appropriate and the examples above are not exhaustive.

TRBC1, TRBC2, TRGC1 and/or TRGC2 DNA or RNA or protein may be detected in cells using flow cytometry. Such methods may use antibodies which are able to distinguish between the different beta and gamma chain constant regions, or they may use labelled DNA or RNA probes which can distinguish between the different beta and gamma chain constant regions.

The phrase "specific detection reagent" is used herein to refer to a reagent which is capable of distinguishing between TRBC1, TRBC2, TRGC1 and/or TRGC2 at the DNA, RNA or protein level, and includes for example PCR primers, oligonucleotide probes and antibodies.

Proteomic analysis of populations of T-cells may also be used to detect TRBC1, TRBC2, TRGC1 and/or TRGC2 protein in T-cell populations.

The T cell receptor beta or gamma chain constant region (one of TRBC1, TRBC2, TRGC1 or TRGC2) may be detected using DNA or RNA sequencing techniques, for example Whole Transcriptome Shotgun Sequencing (RNAseq).

In addition to TRBC1, TRBC2, TRGC1 and/or TRGC2, the expression of other markers may also be detected, particularly by means of immunohistochemistry, in situ hybridisation and flow cytometry, for example, but not limited to, CD2, CD3, CD5, CD4, CD7, CD8 or CD30, CD56, granzyme, perforin, Mib-1, Ki-67, PD1, CD10, CXCL13 and bcl6. Detection of such other markers may be undertaken concurrently with the detection of TRBC1, TRBC2-1,TRGC1, and/or TRGC2.

An advantage of detecting TRBC1, TRBC2, TRGC1 and/or TRGC2 DNA or RNA or protein by in situ hybridisation, immunohistochemistry or flow cytometry is that other factors such as the cell morphology and immunophenotype and, in the case of in situ hybridisation and immunohistochemistry, the architectural distribution pattern of T cells expressing a particular constant region may be detected at the same time.

In an embodiment more than one, preferably 2, 3, 4 or more, different oligonucleotides unique to each constant region are employed for the purposes of in situ hybridisation in the method of the invention. This has two advantages: first it increases the sensitivity of the method and second it increases the intensity of the signal.

The variant T cell receptor beta or gamma chain constant region may be detected using antibodies, bispecific antibodies, antibody mimetics or fragments or variants thereof. The method of determining the ratio of TRBC1:TRBC2 or of TRGC1:TRGC2 in a T cell population may use antibodies, antibody mimetics or fragments thereof. TRBC1/TRBC2 and TRGC1/TRGC2 are very similar at the protein level, but antibodies can distinguish their protein sequences. Antibodies may be used as specific detection reagents or detection reagent in addition to, or instead of, the oligonucleotide specific detection reagents in immunohistochemical techniques.

The method may comprise determining the percentage of T cells in a particular population that express a specific T cell receptor beta or gamma chain constant region. Expression of one or more of TRBC1, TRBC2, TRGC1 and TRGC2 may be detected in a population of T cells. The percentage of T cells in the population that express the detected T cell receptor constant region (TRBC1, TRBC2, TRGC1 and/or TRGC2) may be determined. Expression of two or more out of TRBC1, TRBC2, TRGC1 and TRGC2 may be detected. Expression of three or more out of TRBC1, TRBC2, TRGC1 and TRGC2 may be detected. Expression of all four of TRBC1, TRBC2, TRGC1 and TRGC2 may be detected. Preferably the expression of at least TRBC1 and TRBC2, and/or TRGC1 and TRGC2 is determined.

The method may comprise determining the ratio of cells expressing TRBC1 to cells expressing TRBC2 in the T cell population or determining the ratio of cells expressing TRGC1 to cells expressing TRGC2 in the T cell population or both.

The ratio of TRBC1 to TRBC2 or the ratio of TRGC1 to TRGC2 may be determined by specifically detecting one of the constant regions from a pair and comparing the number of cells where a marker is detected with the number of cells where no marker is detected. Alternatively both TRBC1 and TRBC2 may be detected and/or both TRGC1 and TRGC2 may be detected and the ratio of TRBC1 to TRBC2 or the ratio of TRGC1 to TRGC2 or both may be determined.

Determination of the degree of monotypia in a population of T cells may be used as a tool to provide information about whether a T cell population is an inflammatory or a neoplastic T cell population. A T cell population that has a high degree of monotypia, compared to what is expected for T cell populations in that tissue type or that individual, may be diagnostic of it being a neoplastic T cell population. This may indicate the need for further investigation using other indicators to determine whether a T cell neoplasm is present, or it may be used alone to diagnose a T-cell neoplasm definitively.

The percentage of TRBC1, TRBC2, TRGC1 and/or TRGC2 or the ratio of TRBC1:TRBC2 or of TRGC1:TRGC2 in a population of T cells (a test population of T cells) may be compared to the percentage of TRBC1, TRBC2, TRGC1 and/or TRGC2 or the ratio of TRBC1:TRBC2 or of TRGC1:TRGC2 in a reference population of T cells. The reference population of T cells may be a population of T cells that is known to be an inflammatory T cell population. The reference population of T cells may be a population of T cells that is known to be a neoplastic T cell population. The reference population of T cells may be a population of T cells that is known to be a non-neoplastic or non-inflammatory T cell population. The reference population of T cells may be a population of T cells from the same subject as the test population or from a different subject from the test population. The reference population of T cells may be from a similar tissue type or a similar subject. The reference population of T cells may also include an immortalised T cell lymphoma line grown in vitro.

A high level of monotypia in a test population of T cells, compared to in a reference population of T cells, may indicate that the population of T cells is a neoplastic T cell population rather than an inflammatory T cell population. It is possible for the ratio of TRBC1:TRBC2 or of TRGC1:TRGC2 to be altered in an inflammatory population of T cells due to clonal expansion of T cells in response to an antigen. Therefore, information about the ratio of TRBC1:TRBC2 and/or of TRGC1:TRGC2 in a population of T cells may be used alone or be combined with other information about the cells to determine whether a T cell population is an inflammatory T cell population or a neoplastic T cell population. For example the other information may include whether TRBC1 (or TRBC2) cells appear atypical/pleomorphic (eg have large or abnormal nuclei or mitoses), or the location of the T cells (eg in the epidermis or dermis of skin biopsies), or what percentage of the T cells in the population stain with other markers (including, but not limited to, CD2, CD3, CDS, CD4, CD7, CD8 or CD30, CD56, granzyme, perforin, Mib-1, Ki-67, PD1, CD10, CXCL13 and bcl6).

The ratio of TRBC1:TRBC2 or of TRGC1:TRGC2 may be any ratio and may depend on the specific circumstances of the T cell population. The ratio of TRBC1:TRBC2 or of TRGC1:TRGC2 in a neoplastic population of T cells may be further from 1:1 than the ratio of TRBC1:TRBC2 or of TRGC1:TRGC2 in an inflammatory T cell population. It is possible for both inflammatory and neoplastic T cell populations to have a ratio of TRBC1:TRBC2 or of TRGC1:TRGC2 that is not 1:1.

A polytypic population of T cells may have a ratio closer to 1:1 than a monotypic population of T cells. A population of T cells that appears polytypic may be an inflammatory T cell population.

A monotypic population of T cells may have a ratio further from 1:1 than a polytypic population of T cells. A population of T cells that appears monotypic may be a neoplastic T cell population.

In an embodiment of the invention if more than about 60%, or more than about 70%, or more than about 80%, or more than about 85%, or more than about 90%, of the T-cells in a sample express a particular beta or gamma constant chain, be that TRBC1, TRBC2, TRGC1 or TRGC2, then the population may be defined as monotypic and likely to be clonal. If a population is defined as monotypic, and therefore is likely to be clonal, it may also be defined as neoplastic. In an embodiment, if a population of T cells has more than 80% of its cells expressing a particular beta or gamma TCR constant chain region, then the population may be considered neoplastic.

A population of T cells may be a group of T cells. The population of T cells may be in a sample or isolated from a sample from a subject. The population of T cells may be in a sample or isolated from a sample of a particular tissue or of blood or bone marrow. A population of T cells may be some or all of the T cells in a particular tissue. A population of T cells may be some or all of the T cells in a sample taken from a particular tissue and/or a particular subject.

The subject may be a human or non-human mammal. A non-human mammal may include one or more of a mouse, rat, cat, dog, sheep, goat, cow, horse, primate, alpaca or llama.

A sample may be all or part of a tissue or fluid or suspension from a subject or of a blood sample, lymph node aspirate or bone marrow aspirate specimen. A sample may be a piece of a tissue. A sample may be tissue from a biopsy. A sample may be part or all of a tissue, lymph node or part or all of a lump, swelling or tumour. The sample may be from a tissue or part of a tissue that appears macroscopically normal.

The tissue may be any tissue sample, or blood sample or bone marrow sample or a part thereof. The tissue may be part or all of a lymph node. The tissue may, for example, be skin, gastrointestinal tract, bone marrow, lung, liver, spleen, fat, kidney or blood. Since lymphomas, leukaemias and inflammatory T cell infiltrates can occur anywhere in the body the tissue may be any tissue and the sample may be a solid or fluid sample from any tissue.

TRBC1, TRBC2, TRGC1 and/or TRGC2 may be detected in the population of T cells that are within a tissue sample (as described above). TRBC1, TRBC2, TRGC1 and/or TRGC2 may be detected in a population of T cells that have been separated from the tissue before testing. TRBC1, TRBC2, TRGC1 and/or TRGC2 protein, DNA or RNA may be detected in a protein, DNA or RNA sample extracted from a sample or a population of T cells.

In a further aspect the present invention provides a method of determining whether a population of T cells is a neoplastic T cell population or an inflammatory T cell population, wherein the method comprises determining the ratio of TRBC1:TRBC2 and/or of TRGC1:TRGC2, in a T cell population using any method that is able to quantify or otherwise define expression of TRBC1, TRBC2, TRGC1 and/or TRGC2 and may be used to provide an indication of the percentage of T cells that express a T cell receptor with TRBC1, TRBC2, TRGC1 and/or TRGC2.

Preferably if, in the population of T-cells studied, more than 60%, 70%, 80%, 85%, 90% of the T-cells express TRBC1 then the sample may be defined as neoplastic. Preferably if in the population of T-cells studied more than 60%, 70%, 80%, 85%, 90% or more of the express TRBC2 then the sample may be defined as neoplastic. Preferably if in the population of T-cells studied more than 60%, 70%, 80%, 85%, 90% or more of the express TRGC1 then the sample may be defined as neoplastic. Preferably if in the population of T-cells studied more than 60%, 70%, 80%, 85%, 90% or more of the express TRGC2 then the sample may be defined as neoplastic. Preferably if, in the population of T-cells studied, more than 60%, 70%, 80%, 85%, 90% of the T-cells express a the same TCR constant region then the sample may be defined as neoplastic.

In a further aspect the present invention provides a pair of oligonucleotides suitable for use in a PCR reaction to specifically detect TRBC1, TRBC2, TRGC1, or TRGC2. The pair of oligonucleotides may be used in determining the ratio of TRBC1:TRBC2 or of TRGC1:TRGC2 in a T cell population. The oligonucleotides may be suitable for use in a PCR reaction to determine the ratio of TRBC1:TRBC2 or of TRGC1:TRGC2 in a T cell population.

The pair of oligonucleotides may specifically detect TRBC1 but not TRBC2. The pair of oligonucleotides may specifically bind to and amplify a part or all of TRBC1 but not TRBC2. One or both of the pair of oligonucleotides may bind within TRBC1 but not TRBC2. One or both of the pair of oligonucleotides may bind within the 3' untranslated region of TRBC1, for example may bind within the sequence set out in SEQ ID NO: 1. The pair of oligonucleotides that specifically bind to and amplify part or all of TRBC1 but not TRBC2 may have the sequences set out in SEQ ID NO:9 and SEQ ID NO: 10.

The pair of oligonucleotides may specifically detect TRBC2 but not TRBC1. The pair of oligonucleotides may specifically bind to and amplify a part or all of TRBC2 but not TRBC1. The pair of oligonucleotides may bind within TRBC2 but not TRBC1. One or both of the pair of oligonucleotides may bind within 3' untranslated region of TRBC2, for example may bind within the sequence set out in SEQ ID NO: 2. The pair of oligonucleotides that specifically bind to and amplify part or all of TRBC2 but not TRBC1 may have the sequences set out in SEQ ID NO:11 and SEQ ID NO: 12. As the 3' untranslated regions (3'UTR) of TRBC1 and TRBC2 differ from each other oligonucleotides may be designed to bind within the 3'UTR to distinguish between TRBC1 and TRBC2.

In a further aspect the present invention provides an oligonucleotide or a set of oligonucleotides that are able to specifically bind to only one of TRBC1, TRBC2, TRGC1, or TRGC2. The oligonucleotide(s) may be directly or indirectly labelled and detectable by chromogenic, fluorescent, radioisotopic or other means. The oligonucleotide may be suitable for use in in situ hybridisation. An oligonucleotide of the present invention may bind to any part of the DNA or RNA sequence of TRBC1, TRBC2, TRGC1, or TRGC2 that differs from the others. The sequences of TRBC1, TRBC2, TRGC1, or TRGC2 shown in the present application may therefore be used to design oligonucleotides of any length provided that they specifically bind to the sequence of only one of TRBC1, TRBC2, TRGC1, or TRGC2. In an embodiment at least 2, or at least 3, or at least 4 or more oligonucleotides are used to detect each of TRBC1, TRBC2, TRGC1, or TRGC2.

The oligonucleotide may have a sequence selected from any of the group comprising SEQ ID NO. 9, 10, 11 or 12, or a sequence having 80%, 90%, 95%, or 99% identity to SEQ ID NO. 9, 10, 11 or 12 or the complement of any of these sequences.

The oligonucleotides probes may include one or more, preferably at least 2, 3, or 4 probes, that bind to sequences with either Sequence ID No: 15 (part of TRBC1) or Sequence ID No: 16 (part of TRBC2).

In order to detect TRBC1 one or more oligonucleotide probes of the sequence of Seq ID Nos: 17 to 22 may be used. Preferably 17 and 18 are used. Preferably one or more, 2 or more, 3 or more, or all of Seq ID Nos: 19 to 22 are used.

In order to detect TRBC2 one or more oligonucleotide probes of the sequence of Seq ID Nos: 23 to 29 may be used. Preferably oligonucleotide probes with sequence of one or more, 2 or more, or all, of Seq ID Nos: 23 to 25 are used. Alternatively, oligonucleotide probes with sequence of one or more, 2 or more, 3 or more, or all of Seq ID Nos: 26 to 29 are used. Alternatively, oligonucleotide probes with sequence of one or more, 2 or more, 3 or more, 4 or more, or all, of Seq ID Nos: 23 to 29 are used.

The oligonucleotide probes are preferably labelled, directly or indirectly, and binding may be detected by eye or digitally, for example under a microscope by the human eye or digitally, such as by using flow cytometry or other means of digital detection.

In a further aspect the present invention provides a diagnostic reagent comprising an oligonucleotide or an antibody that specifically binds to only one of TRBC1, TRBC2, TRGC1, or TRGC2. The diagnostic reagent may also comprise a detectable label, for example a coloured, fluorescent, radioactive, specific binding, specific size reagent.

TRBC1 and TRBC2 nucleotide sequences differ at the sequences shown in larger font in FIG. 7. An oligonucleotide, set of oligonucleotides, specific detection reagent or reagent that binds to part or all of this sequence or includes this sequence may be used to specifically detect only TRBC1 or only TRBC2 but not both.

TRGC1 and TRGC2 nucleotide sequences differ at the sequence shown in larger font in FIG. 8. TRGC2 has one or more additional exons compared to TRGC1. An oligonucleotide, set of oligonucleotides, probe or reagent that binds to part or all of this additional sequence or includes this sequence may be used to specifically detect only TRGC1 or only TRGC2 but not both.

In a further aspect the present invention provides use of a set of oligonucleotides to determine the ratio of TRBC1: TRBC2 or of TRGC1:TRGC2 in a T cell population.

The oligonucleotides may have more than 60%, more than 70%, more than 80%, more than 90%, more than 95%, more than 98%, more than 99% or 100% sequence identity to a sequence that is complementary to the sequence that it specifically binds to.

The set of oligonucleotides may comprise one or more of the oligonucleotides described herein as having the sequence of Seq ID Nos: 9 to 12 and 17 to 29.

The oligonucleotides must be long enough to specifically bind to their target DNA or RNA sequence. The oligonucleotides may be between 5 and 50 nucleotides in length, between 10 and 40 nucleotides in length, between 15 and 30 nucleotides in length, or between 20 and 25 nucleotides in length.

For specific binding, longer oligonucleotides between 50 and 100 nucleotides, or between 100 and 1000 nucleotides, or between 200 and 800 nucleotides, or between 500 and 700 nucleotides in length may be used.

Preferably the oligonucelotides are labelled directly or indirectly to allow visualisation of binding.

In a further aspect the present invention provides one or more antibodies, antibody mimetics, bispecific antibodies or fragments thereof that specifically bind to one polypeptide selected from TRBC1, TRBC2, TRGC1 and TRGC2. The antibody may bind to either TRBC1 or TRBC2 but not both. The antibody may bind to either TRGC1 or TRGC2 but not both. The antibodies may be used to distinguish expression levels of each of these proteins at the protein level. The antibodies may be used to quantify expression of a pair of alternative constant regions and thus to determine the ratio of TRBC1:TRBC2 or of TRGC1:TRGC2 in a T cell population. The antibodies or antibody fragments or mimetics may be modified or labelled. The antibodies may be polyclonal antibodies. The antibodies may be monoclonal antibodies. The antibodies may be suitable for use in immunohistochemistry. An antibody of the present invention may bind to a region of one of TRBC1, TRBC2, TRGC1, or TRGC2 that differs from the others. A likely binding site on TRBC1, TRBC2, TRGC1, or TRGC2 for an antibody of the present invention may be identified by comparing the polypeptide sequences of TRBC1, TRBC2, TRGC1, or TRGC2 and identifying regions of difference.

In a further aspect the present invention provides the use of an oligonucleotide or an antibody according to the present invention in the investigation of T cell monotypia.

A method of the present invention may be an in vitro method. A method of the present invention may be performed in cell culture. A method of the present invention may be performed on a solid or liquid cytological sample or tissue aspirate. A method of the present invention may be an in vivo method.

An oligonucleotide of the present invention may be attached directly to a label or via several layers. For example an oligonucleotide specific detection reagent may be linked to a fluorescent, chromogenic or other form of label using layers of branched DNA polymers which amplify the signal. The label may be a fluorescent, chromogenic, radioactive or other label.

The present invention further provides, use of an oligonucleotide, peptide or antibody specific detection reagent to determine the ratio of TRBC1:TRBC2 or of TRGC1: TRGC2 in a T cell population.

The present invention further provides an oligonucleotide or a set of oligonucleotides according to the present invention, a pair of oligonucleotides according to the present invention or an antibody according to the present invention for use in medicine. An oligonucleotide or antibody according to the present invention may bind selectively to T cells expressing a selected one of the T cell receptor constant regions TRBC1, TRBC2, TRGC1 or TRGC2. An oligonucleotide or antibody or other therapeutic modality according to the present invention may be used in a treatment to target T cells that express a T cell receptor constant region selected from TRBC1, TRBC2, TRGC1 or TRGC2. This may be useful in the treatment or prevention of lymphoma or transplant rejection, an autoimmune disease or an inflammatory disease as T cells expressing a particular one of the T cell receptor constant regions may be inhibited or destroyed selectively while leaving T cells expressing the other T cell constant region unaffected. This limits the amount of immune suppression of the treatment. Once T cells expressing a particular T cell receptor constant region are identified, by the methods of the present invention or by other methods, as being the result of an unwanted clonal expansion T cells expressing the constant region that has been identified may be selectively targeted by medicaments comprising specific detection reagents of the present invention.

The present invention further provides, a kit comprising one or more oligonucleotide, peptide or antibody probes of the present invention, and instructions to use the probes and/or kit to determine the level of expression of one or more of TRBC1, TRBC2, TRGC1 and TRGC2 in a population of T-cells, or in material extracted therefrom.

The kit may further comprise a negative control oligonucleotide or probe. The kit may be intended for use with in situ hybridisation techniques or PCR technicques. It may be used with an RNAscope® assay or with other proprietary detection reagents from any manufacturer.

The present invention further provides a method of diagnosis comprising the use of an oligonucleotide, peptide or antibody probe of the present invention to obtain an indication of the monotypia or clonality of a T cell population. The method may comprise determining the ratio of TRBC1:TRBC2 or of TRGC1:TRGC2 in a T cell population. The method may comprise use of a probe to visualise T cells expressing one or more of TRBC1, TRBC2, TRGC1, TRGC2 in a T cell population. The method may comprise performing in situ hybridisation or immunohistochemistry on a sample using oligonucleotide probes or antibody probes. The method may comprise performing PCR on a sample using TRBC1, TRBC2, TRGC1 or TRGC2 specific oligonucleotide probes.

The invention further provides a method for detecting T-cell monotypia, the method comprising:
I) obtaining a sample containing T-cells from a subject;
II) using directly or indirectly labelled oligonucleotides to determine the level of expression of TRBC1 and TRBC2, and/or TRGC1 and TRGC2, in the T-cells obtained in I;
III) detecting signal associated with oligonucleotide probe hybridisation;
IV) concluding there is T-cell monotypia, indicative of clonality, if more than about 60%, 70%, 80%, 85% or 90% of the T-cells express the same constant region.

The method may further comprise concluding that a sample contained neoplastic T-cells if T-cell monotypia, indicative of clonality, is observed. Preferably to conclude T-cell monotypia as an indication of clonality at least 80% or more of the T-cells must express the same T-cell receptor constant region.

The binding of one or more oligonucleotides to the cells in the sample may be determined by in situ hybridisation.

The method of the invention may therefore be used to diagnose a neoplasm. It may also be used to monitor disease progression and/or response to therapy and/or remission status by looking at changes over time in the T-cell TCR constant region expression pattern. It may also be used to monitor immune responses for indications of whether they are monoclonal. These immune responses may be natural or manipulated by therapies of various sorts, e.g., T-cell responses to tumours with or without treatment with medications such as ipilimumab; T-cell responses in bone marrow and other organs following bone marrow transplantation; T-cell responses in autoimmune conditions with or without treatments and T-cell responses in infectious diseases such as tuberculosis, leprosy and viral infections.

In another aspect of this invention, T-cells expressing a T-cell constant region selected from TRBC1, TRBC2, TRGC1 and TRGC2 may be specifically targeted to augment or modulate the behaviour or function of those T-cells for therapeutic or experimental (research) purposes. Methods for specific targeting may include specific oligonucleotides, specific antibodies, bispecific antibodies, antibody mimetics, antibody fragments or variants thereof or any other specific detection reagent.

The invention may further provide a method of treating a neoplastic condition, for example by using the probes to target the cells and deliver toxic agents to the cells Alternatively, the invention could be used to mark cells in a population that are neoplastic which could then be removed from the population, for example by using FACS, and the population of cells without the neoplastic cells could then be returned to the subject. This could be used to treat lymphomas or leukaemias by treating bone marrow samples in this way.

The skilled man will appreciate that preferred features of any one embodiment and/or aspect and/or claim of the invention may be applied to all other embodiments and/or aspects and/or claims of the invention.

There now follows by way of example only a detailed description of the present invention with reference to the accompanying drawings, in which;

FIG. 1—shows regions of post-splice mRNA including sequence differences between TRBC1 and TRBC2. The end of the last exons are shown in bold, the 3' UTR is shown in normal font and the polyadenylation site (AATAA) is underlined. The site where the reverse primers (shown in FIG. 2) bind is highlighted in larger font, underlined and bold.

FIG. 2—shows primers to amplify TRBC1 and TRBC2. In principle, many other regions containing the 3' untranslated RNA could be used as a site for primer or specific detection reagent binding. For example, all or some of the 3'UTR could be used or the 3'UTR could be included within specific detection reagents which bind larger regions of TRBC1 and TRBC2. In this example, the reverse primers bind at the sites shown in larger font in FIG. 1, while the forward primers bind upstream in the coding region.

Figure 4:
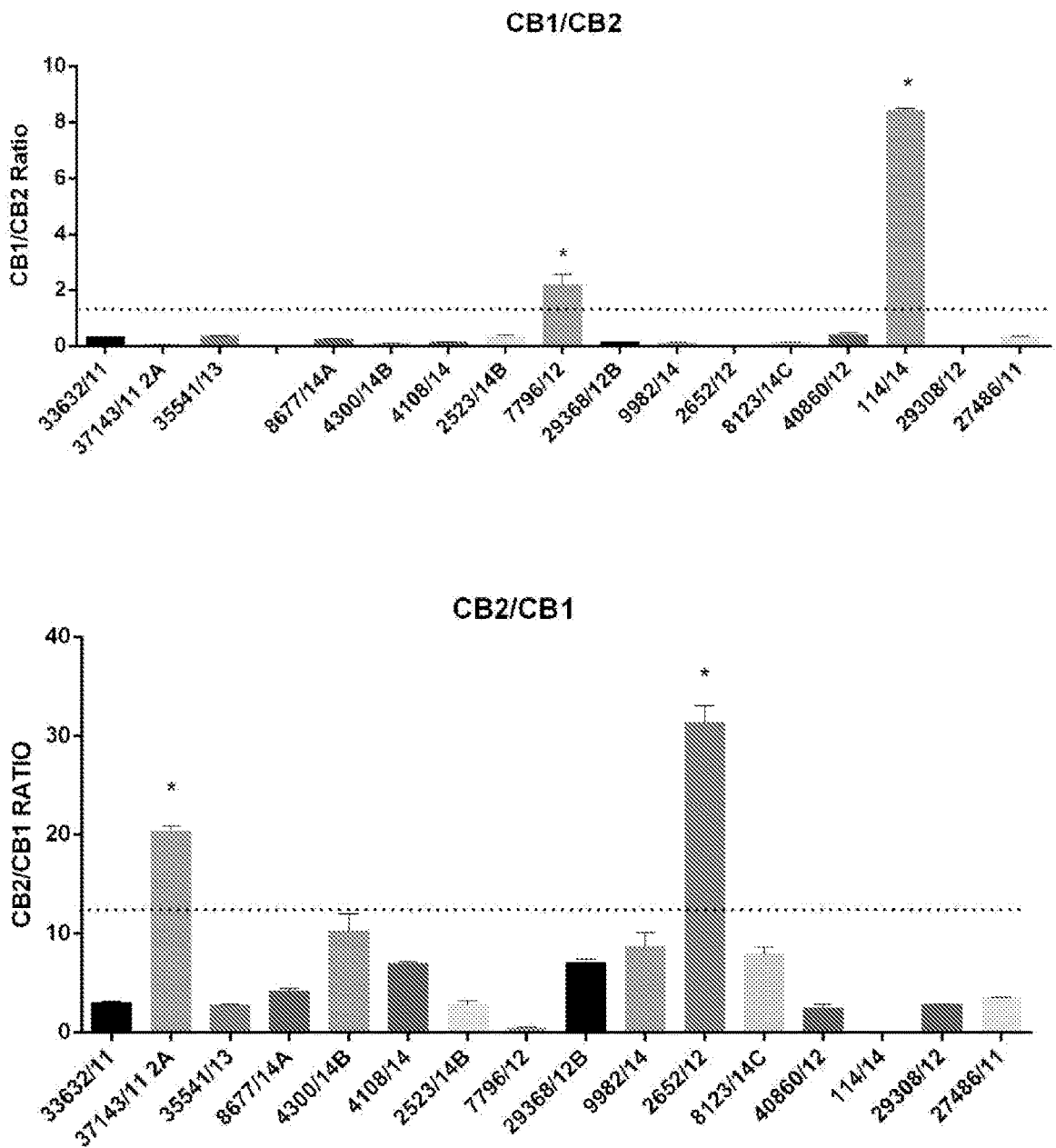

FIG. 3—shows results of TRBC1 and TRBC2 PCR from two polyclonal T cell populations (C12 and C14) and one clonal population (38), showing the latter expresses TRBC2 only, FIG. 4—shows the results of quantitative rtPCR for TRBC1 (CB1) and TRBC2 (CB2) from samples of RNA isolated from paraffin-embedded sections of reactive tissue and T cell lymphoma tissue, *T cell lymphoma samples. Above dotted line represents P<0.05, FIG. 5—shows regions of protein diversity between TRGC1 and TRGC2. The amino acids encoded by TRGC2 additional exon is underlined.

FIG. 6 shows the protein sequence of TRBC1 (SEQ ID NO: 5) and the protein sequence of TRBC2 (SEQ ID NO: 6)

FIG. 7 shows the nucleotide sequence of TRBC1 (SEQ ID NO: 3) and TRBC2 (SEQ ID NO: 4). The sites where the oligonucleotides of FIG. 2 bind are underlined. The principle area where TRBC1 and TRBC2 differ in sequence is indicated in larger font. The tga (TRBC1) or tag (TRBC2) stop codon and the main aataaa polyadenylation signal are indicated with italics and underline.

FIG. 8 shows the nucleotide sequence of TRGC1 and TRGC2. The area where TRBC1 and TRBC2 differ in sequence is indicated in larger font. TRGC2 has an additional exon compared to TRGC1. The taa stop codon and the main aataaa polyadenylation signal are indicated with underline.

Figure 9A:
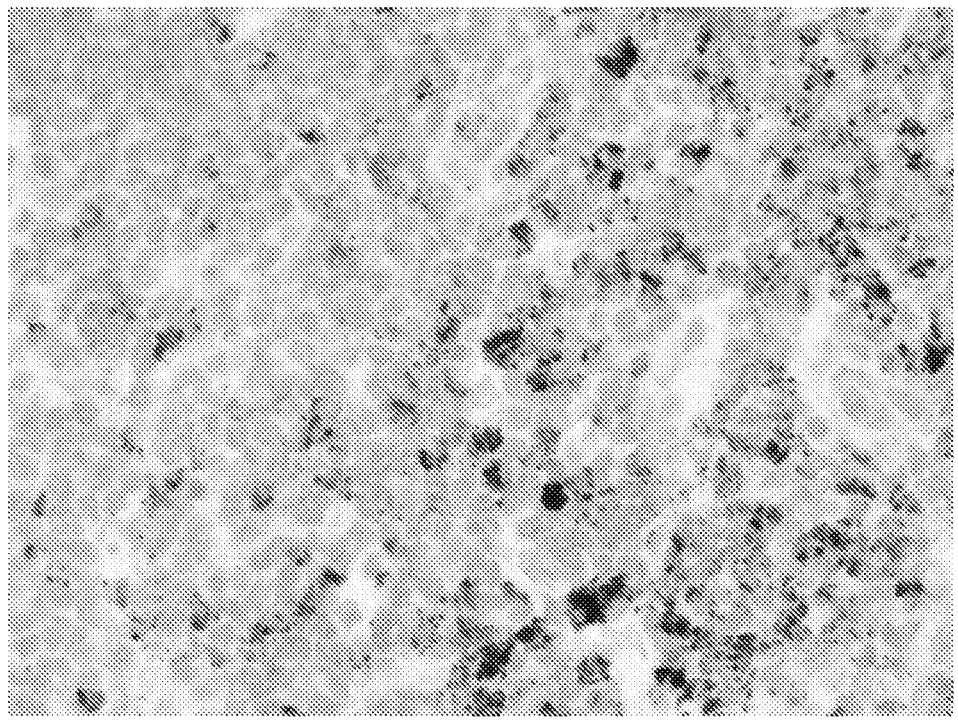
Figure 9B:
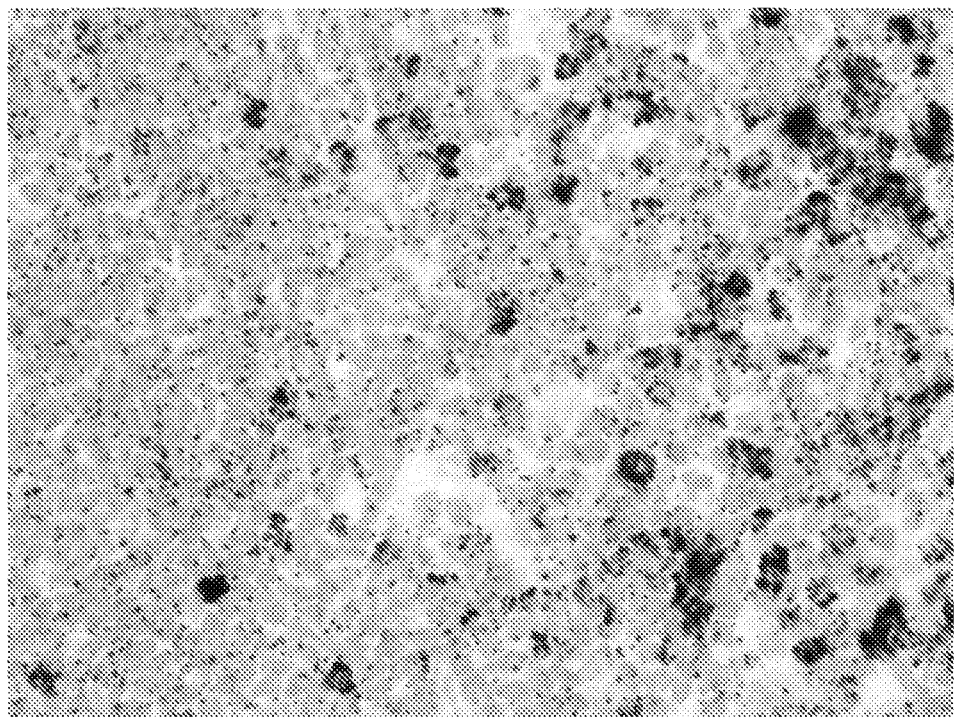

FIGS. 9A and 9B demonstrate that the oligonucleotide probes according to the invention show positive staining in non-neoplastic (benign) lymph node samples.

FIG. 9A shows positive staining with probes directed to TRBC1 and FIG. 9B shows positive staining with probes directed to TRBC2.

FIG. 10 demonstrates that oligonucleotide probes according to the invention can distinguish between clonal cell lines, more specifically in Jurkat cells that exclusively express TRBC1.

FIG. 11 further demonstrates that oligonucleotide probes according to the invention can distinguish between TRBC expression in a clonal cell line, more specifically CEM cells that exclusively express TRBC2. In this Figure TRBC2 is detected using the probes of Seq ID nos: 26 to 29.

Figure 12:
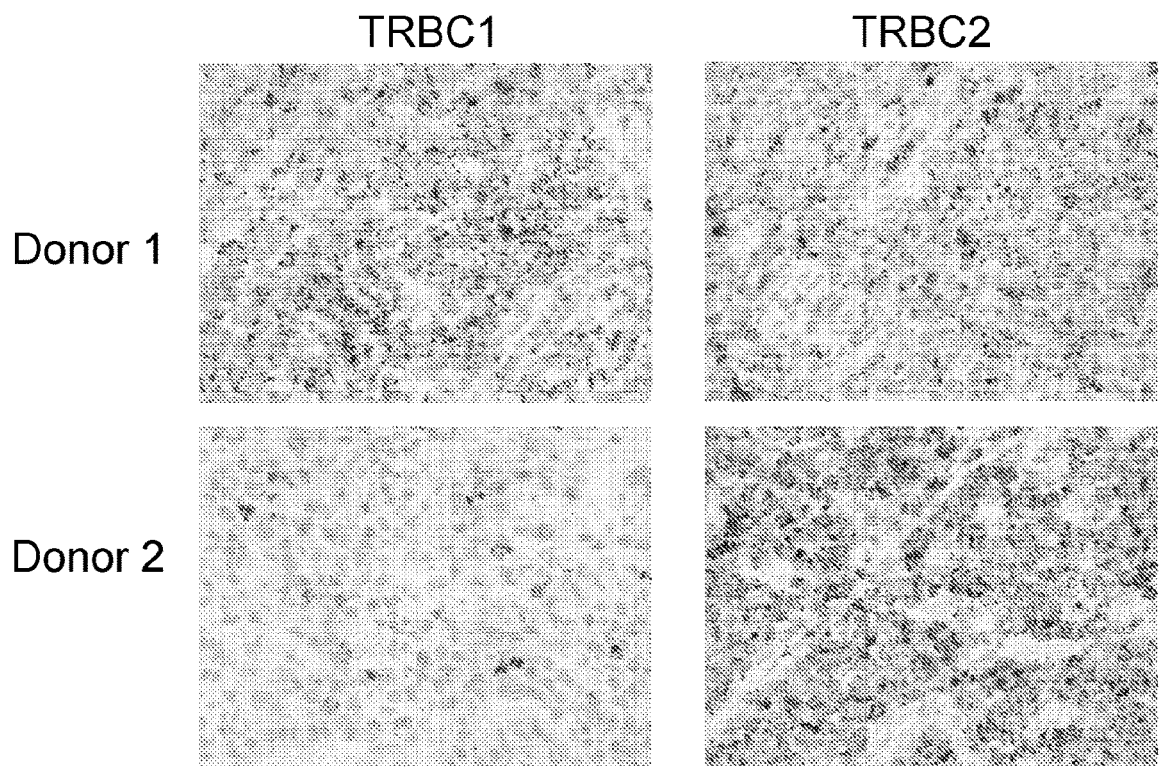

FIG. 12 demonstrates that oligonucleotide probes according to the invention can detect lymphoma cells using in situ hybridisation.

Figure 13:
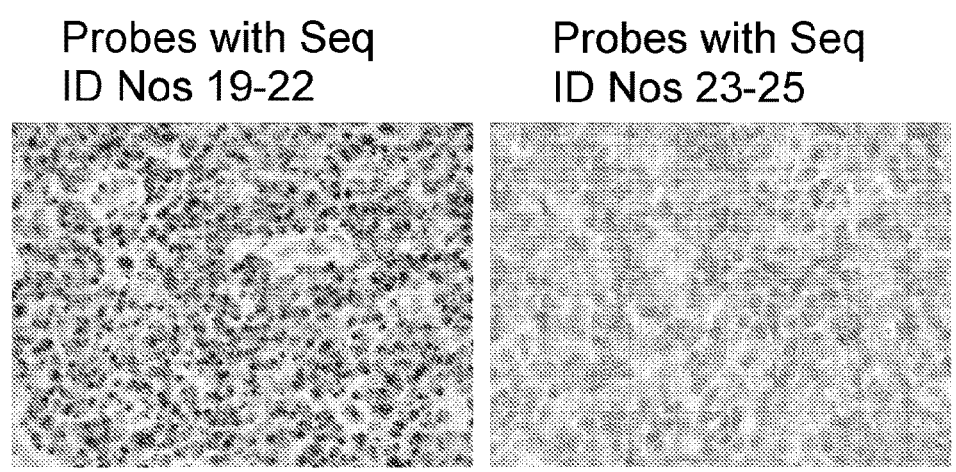

FIG. 13 further demonstrates that oligonucleotide probes according to the invention can detect lymphoma cells using in situ hybridisation. In this Figure TRBC1 is detected using the probes of Seq ID nos: 19 to 22 and TRBC2 is detected using the probes of Seq ID nos: 26 to 29.

FIGS. 14 and 15 demonstrate that TRBC1 and TRBC2 probes according to the invention both bind to non-neoplastic, benign, T-cell populations.

FIG. 16 details the sequences of various oligonucleotide probes used in the present invention.

FIG. 17 details where in TRBC2 oligonucleotides with the sequence of Seq ID Nos: 26 to 29 are located in the reversed and complemented target sequence.

FIG. 18 details where in TRBC1 oligonucleotides with the sequence of Seq ID Nos: 19 to 22 are located in the reversed and complemented target sequence.

The overall structure of the T cell receptor determines its specificity for binding to antigen presented by MHC or MHC-like molecules. T cells can express alpha-beta T cell receptors or gamma-delta T cell receptors. The beta chain comprises one of two alternative, but very similar, constant regions referred to as TRBC1 and TRBC2. Similarly, the gamma chain comprises one of two very similar constant regions referred to as TRGC1 and TRGC2. In a population of T cells some of the T cells have receptors with one form of each of these constant regions and some T cells have receptors with the other form of each of these constant regions. Therefore an alpha-beta expressing T cell will express one of TRBC1 or TRBC2 as the constant region of the beta chain. Similarly a gamma-delta expressing T cell will express one of TRGC1 or TRGC2 as the constant region of the gamma chain.

The differential expression of each of these constant regions could be used as a method to help determine T cell monotypia and clonality and therefore distinguish inflammatory, also known as reactive or benign, T cell infiltrates from neoplastic, also known as malignant or lymphomatous or leukaemic T cell infiltrates.

The protein sequences of human TRBC1 and TRBC2 differ by only a few amino acids which makes them very difficult to differentiate. The RNA sequences differ only slightly within the coding region, however in this invention differences in the 3' untranslated region are used to differentiate TRBC1 and TRBC2. The mRNA sequences of the 3'untranslated regions of TRBC1 and TRBC2 common alleles are shown in FIG. 1. The sequences are from the specialist IMGT database, but it is of note that in some publications and sequence submissions, authors have referred to the sequence names the other way around. The TRBC1 and TRBC2 used are presented in FIG. 1, where the highlighted sequence represent differences which can be used as a means to investigate TRBC1 and TRBC2 expressing T cell populations.

The 3'UTR of TRGC1 and TRGC2 alleles are identical but there are differences in the coding region, an example of which is shown in FIG. 5. TRCG2 alleles all have one or two additional exons compared to TRGC1 alleles. Highlighted differences in the amino acid sequence or the mRNA sequence of TRGC1 and TRGC2 can be used to differentiate between them.

Using PCR to Distinguish Between T-cell Receptor Constant Regions

PCR primers were designed (FIG. 2) that can be used to specifically amplify parts of the unique 3'untranslated regions which differed between TRBC1 and TRBC2. The forward primer binds within the coding region of TRBC1 or TRBC2 and the reverse primers bind in the 3'UTR at the positions shown in larger font in FIG. 1. cDNA was generated from RNA isolated from tissue sections (including paraffin-embedded sections, fresh sections, or frozen sections) or from cells isolated in culture. It was confirmed that using primers where the reverse primer bound within the 3' untranslated region and the forward primer bound upstream that TRBC1 and TRBC2 could be distinguished using rtPCR from cells grown in culture, including clones and polyclonal T cell populations (FIG. 3).

Quantitative rtPCR was used to compare the TRBC1 and TRBC2 ratio in RNA isolated from reactive or neoplastic formalin-fixed paraffin-embedded tissue. There was differential expression of TRBC1 and TRBC2 in all samples, as reactive tissue may contain antigen-specific T cell expansions. However four samples showed TRBC1/TRBC2 ratios that were significantly ($P<0.05$) different to the reactive samples (FIG. 4). All of these were isolated from lymph nodes containing mainly T cell lymphoma. These data confirm that analysis of the ratio of TRBC1 and TRBC2 expression can be used to test T cell populations in culture or in tissues in order to examine their relative monotypia and clonality.

A PCR based approach has been used as validation, but alternatively an in-situ RNA hybridisation or immunohistochemical/immunocytochemical approach could be used to analyse the ratios, as this allows the concurrent generation of architectural, morphological and/or immunophenotypic data and the detection of TRBC1 or TRBC2 in different cell subpopulations (eg CD4+ or CD8+ cells, or cells in different tissue locations eg dermal or epidermal cells in skin biopsies)—this may enhance the ability to further distinguish reactive (or benign or inflammatory) T cell populations from malignant or lymphomatous or neoplastic T cell populations.

Lastly, although the protein sequences of TRBC1 and TRBC2 are similar, monoclonal antibodies that specifically bind to one polypeptide selected from TRBC1, TRBC2, TRGC1 and TRGC2 may be generated that can distinguish TRBC1 from TRBC2 and TRGC1 from TRGC2, potentially allowing determination of differential expression levels at the protein level.

The 3' untranslated RNA region contains differences in RNA sequence that can be used to examine differential levels of expression. In situ or PCR-based detection of RNA could be based on the expression of any region of sequence difference between TRBC1 and TRBC2.

The preliminary studies have used TRBC1 and TRBC2 as the majority of neoplastic human T cell infiltrates (eg lymphomas) are derived from alpha-beta TCR-expressing T cells, but rare neoplastic gamma-delta T cell infiltrates (eg lymphomas) exist. FIGS. 5 and 8 show regions of TRGC1 and TRGC2 that would be amenable to similar differential expression analyses at the protein or RNA levels.

In summary the present experiments show that the ratio of expression of T cell receptor constant region genes can be used to identify whether T cell populations are reactive/inflammatory or neoplastic. Using the 3' untranslated region of TRBC1 and TRBC2 solves the problem that the coding gene sequences are similar, and using methods that detect the 3' untranslated region would therefore be particularly useful in specifically detecting levels of TRBC1 and TRBC2 expression.

RT-PCR Method

RNA extraction and cDNA synthesis from formalin fixed paraffin embedded tissues were performed using RNeasy FFPE Kit (QIAGEN 73504) and SuperScript® III First-Strand Synthesis System (Life Technologies 18080-051) according to the manufacturer's instructions. The following primer sets were designed

```
TRBC1
Forward
                                      (SEQ ID NO: 9)
ACCCTGTATGCTGTGCTGGT;

Reverse
                                      (SEQ ID NO: 10)
GGGATGCAGAGAGGTGAGAG TRBC2
Forward
                                      (SEQ ID NO: 11)
ACCTTGTATGCCGTGCTGGT;

Reverse
                                      (SEQ ID NO: 12)
CTGGGATGGTTTTGGAGCTA ACTIN
Forward
                                      (SEQ ID NO: 30)
GGACTTCGAGCAAGAGATGG;

Reverse
                                      (SEQ ID NO: 31)
AGCACTGTGTTGGCGTACAG
```

Reactions were performed using the Power SYBR® Green PCR Master Mix (4367659) in a 7500 Fast Thermal Cycler (Applied Biosystems). Real-time PCR reaction mixtures were prepared by adding 25 µl SYBR® Green PCR Master Mix, 300 nM primer sets, 10 µl cDNA and H2O (up to 50 µl). RT-PCR conditions were as follows: Enzyme activation (hold) 95° C. for 10 min, 40 cycles of 95° C. for 15 sec and 60° C. for 1 minute.

Using In Situ Hybridisation to Distinguish Between T-cell Receptor Constant Regions and to Diagnose a Neoplastic Condition

EXAMPLE 1

RNAScope to validate levels of expression of TRBC1 & TRBC2 in T-cells can be determined using RNAScope To confirm that RNA was preserved when a biopsy samples was put on a slide, in vitro hybridisation experiments using an RNAScope probe directed against RNA transcripts with a low level of expression, for example PPIB, were undertaken on biopsy samples on slides. The results obtained showed good preservation of RNA in the control experiment.

The next step was to determine if there was a signal using RNAScope (Minca EC et al. J Cutan Pathol. 2015 Feb;42 (2):82-9) and probes for TRBC1 & TRBC2. When labelled probes specific for either TRBC1 & TRBC2 were applied to non-neoplastic (benign) lymph node tissue samples, signals were seen on all slides (FIG. 9). The staining in FIG. 9 is representative of a normal lymph node where the T-cells express a mix of TRBC1 & TRBC2 expression.

To demonstrate that TRBC1/TRBC2 expression can be separately detected, clonal cell lines expressing only TRBC1 (Jurkat cells) or TRBC2 (CEM cells) were stained with the same labelled probes specific for TRBC1 or TRBC2. The results are shown in FIGS. 10 and 11, from which it is clear that T-cells are monotypic for TRBC1 or TRBC2 when they are part of a clonal population, such as the cell lines shown in this case. The results observed in this histological study were supported by RT-PCR analysis.

When the number of cells in the clonal cells lines stained with TRBC1 and TRBC2 were counted the following results were observed:

Individual cell line data (percentage of positive cells):
CEM (TRBC2-restricted by PCR)
TRBC1 0.17 (0.04-0.53) %
TRBC2 95.56% (94.48-96.44)
MOLT-4 (TRBC2-restricted by PCR)
TRBC1 0.06 (0.00-0.37) %
TRBC2 97.06 (96.14-97.77) %
RPMI8402 (TRBC1-restricted by PCR)
TRBC1 86.00 (84.29-87.55)%
TRBC2 22.00 (20.12-24.00) %
Jurkat (TRBC1-restricted by PCR)
TRBC1 90.72 (89.26-92.00) %
TRBC2 3.17 (2.43-4.12) %

All cell lines were scored by 3 observers, each scoring 600 cells for TRBC1 and 600 cells for TRBC2, meaning that 1800 cells were scored altogether per cell line. For all scoring (all cell lines and probe sets taken together), the correlation between results obtained by any pair of observers was between 0.99 and 1.00 (Spearman's). 95% confidence intervals were calculated using the Wilson procedure with a correction for continuity.

Having demonstrated in FIGS. 10 and 11 that TRBC1 and TRBC2 can be used to distinguish different clonal neoplastic cell lines, the question was to demonstrate that the principle could translate to patient samples and could be used, for example, for the diagnosis of lymphoma. The difficulty is distinguishing lymphoma cells from associated reactive (non-neoplastic) T-cells, which can, in some cases, represent >50% of the infiltrate. Reactive T-cells are non-clonal and should be a roughly equal mixture of TRBC1 and TRBC2 expressing cells. However, sometimes lymphoma cells are identifiable morphologically (big, pleomorphic etc). By using the method of the invention to stain TRBC1 and TRBC2 cells in situ, the results can be combined with morphological analysis to give a diagnosis. This is illustrated in FIGS. 12 and 13, which both demonstrate that T-cell lymphomas appear to predominantly express only one TRBC type.

As well as examining differential morphology of the T cells expressing each TRBC, it may also be possible to use co-staining with other T cell markers, which is likely to enhance significantly the sensitivity of lymphoma detection.

FIG. 14 further demonstrates the diagnostic properties of the invention. In FIG. 14 non-neoplastic benign lymph node tissue is stained with TRBC1 probes (probes with Seq ID nos: 17 and 18) and TRBC2 probes (probes with Seq ID nos: 26 to 29). The results show that approximately half of the T-cells in the paracortex (T-cell area) shown are positive with each probe set (brown dots, DAB detection). At the top of each image, there is a clearly defined elongated negative area, which is a lymph node cortical sinus. These rarely contain T-cells.

FIG. 15 shows similar result to FIG. 14 but using different probe sets and different detection methodology. Hybridisation was performed in a formamide and SSC buffer on a fully automated Ventana Discovery Ultra Immunostainer (Ventana Medical Systems Inc, Tuscon, AZ). The cocktails of probes (TRBC1 probes with sequences of Seq ID nos: 19 to 22 and TRBC2 probes with sequences of Seq ID nos: 26 to 29) were used for hybridisation at between 37C and 46C. Three stringency washes were performed using 0.1% SSC at between 37C and 48C. Probes were digoxygenin labelled and were detected by means of an HRP-tagged anti-digoxygenin mouse monoclonal antibody with a proprietary multimer amplification system attached (Ventana Medical Systems Inc, Tuscon, AZ). This was followed by tyramide amplification, depositing the hapten BF (Rimsza et al. Diagnostic Pathology 2014 9:144), which was detected with an HRP-tagged mouse anti-BF antibody. Development with diaminobenzidine followed, leaving brown substrate at all sites where probes were bound. Sections were counterstained with haematoxylin and mounted in Depex. Again approximately half of the T-cells in the paracortex (T-cell area) shown are positive with each probe set (brown dots, DAB detection). At the top of each image, there is a clearly defined elongated negative area, which is a lymph node cortical sinus in TRBC1 staining and a blood vessel in TRBC2 -both rarely contain T-cells.

There now follows examples of how the present invention could be used to alter and improve current clinical practice in relation to lymphoma and leukaemia.

1. Skin lymphomas (including but not limited to mycosis fungoides; Sezary syndrome; peripheral T-cell lymphoma, not otherwise specified; anaplastic large cell lymphoma; lymphomatoid papulosis; primary cutaneous CD4-positive small/medium-sized pleomorphic T-cell lymphoma).

Skin lymphomas present with appearances, usually red patches, similar to benign inflammatory skin conditions. These are often biopsied but benign conditions and lymphomas are difficult to distinguish by current morphological and immunohistochemical means. PCR-based T-cell receptor gene rearrangement studies may fail or give results that are monoclonal, oligoclonal or polyclonal, which show incomplete correlation with clinical diagnosis, viz lymphomas are often monoclonal, but strong immune responses occurring as part of inflammatory processes may also give monoclonal results. Conversely, polyclonal or oligoclonal results may be more frequently seen in benign inflammatory skin conditions, but a proportion of lymphomas will give polyclonal or oligoclonal results because there is a large benign T-cell population reacting to the lymphoma that obscures any monoclonal result obtained from the lymphoma cells. In all these situations, the difficulty occurs, because the population of cells responsible for producing any clonal peaks in the PCR results cannot be distinguished from other populations. In a high proportion of cases, no conclusive diagnosis is reached, despite these analyses, so radiological investigation and laboratory analysis of blood and bone marrow samples may be undertaken in an attempt to reach a conclusive diagnosis. These additional investigations rarely help and an expectant ("watch and wait") approach is taken. One waits for the patient to return and repeats the biopsy analysis, in the hope of a more conclusive result, and one undertakes radiological investigation and laboratory analysis of blood and bone marrow samples.

TRBC1/2 analysis as described in the present invention would solve this problem. For example, by using oligonucleotides or antibodies according to the invention TRBC1/2 analysis can be applied to a population of cells which may also be defined on the basis of their morphological appearance, immunophenotype (e.g., larger size, expression of CD4 or CD8 or CD30) or other characteristics. If, for example, 90% (or 80% or 70% or 60%) of the CD4+T-cells are TRBC1-restricted (i.e., express TRBC1 not TRBC2), then one may be able to conclude that this is lymphoma rather than a benign inflammatory skin condition and treat the patient with radiotherapy, chemotherapy or other appropriate treatments. It should also be noted that such TRBC1/2 analysis according to the invention may be undertaken cheaply and quickly, in less than 24 hours, while T-cell receptor gene rearrangement studies will take one to several weeks. The present invention provides a more reliable, conclusive and rapid result that can be obtained more cheaply.

2. Small Intestinal Refractory Coeliac Disease/Enteropathy-Associated T-Ccell Lymphoma Coeliac disease is an autoimmune disease, triggered by a T-cell response to the protein gluten, found in barley, rye and wheat. A small percentage of coeliac sufferers develop enteropathy-associated T-cell lymphoma, a condition that is virtually never seen in the absence of coeliac disease. The key difference between coeliac disease and enteropathy-associated lymphoma is that the histological features (lymphocytes in the small intestinal epithelium with damage to small intestinal villi) and symptoms (diarrhoea, abdominal bloating, anaemia, fatigue) of coeliac disease resolve on strict avoidance of dietary gluten, but those of enteropathy-associated lymphoma and refractory coeliac disease (increasingly regarded as an early form of enteropathy-associated lymphoma) do not. However, a proportion of individuals have ongoing exposure to gluten without realising it and their symptoms fail to resolve, despite an apparently gluten-free diet (in which they are unaware of the ongoing gluten exposure). They often undergo duodenal biopsy because there is a suspicion of evolving enteropathy-associated T-cell lymphoma and histological examination and clonality studies are performed on the biopsy. As with the discussions about skin lymphomas above, existing clonality studies do not distinguish reliably distinguish the benign condition, active coeliac disease, from the lymphomatous conditions, refractory coeliac disease/enteropathy-associated lymphoma. Radiological investigation and laboratory analysis of blood and bone marrow samples cannot always assist in this distinction and the patient may be observed and undergo dietary manipulation and further biopsy in an attempt to reach a definitive diagnosis.

As described with reference to skin lymphomas, TRBC1/2 analysis by techniques of the present invention, such as (but not limited to) histology can be specifically applied to a population of cells defined on the basis of their morphological appearance, immunophenotype (e.g., larger size, expression of CD4 or CD8 or CD30) or other characteristics to determine whether there is skewing towards TRBC1 or TRBC2. If, for example, 90% (or 80% or 70% or 60%) of the CD8+ T-cells are TRBC1-restricted (i.e., express TRBC1 not TRBC2), then one can conclude that this is one of the lymphomatous conditions, refractory coeliac disease/enteropathy-associated lymphoma and treat the patient with chemotherapy. The sooner this can be instigated in the aggressive coeliac-associated lymphomas, the better the prognosis. As discussed earlier, the TRBC1/2 analysis of the present invention can be undertaken cheaply and quickly, in less than 24 hours, providing a more reliable, conclusive and rapid result.

3. T-Cell Lymphomas and Leukaemias in Bone Marrow

T-cell large granular lymphocyte leukemia (T-LGL) is a clonal proliferation of CD8+ T lymphocytes, which causes neutropenia (i.e., decreased numbers of neutrophils in peripheral blood), anaemia (i.e., decreased numbers of red blood cells in peripheral blood), and/or thrombocytopenia (i.e., decreased numbers of platelets in peripheral blood). This condition is often associated with autoimmune disorders, especially rheumatoid arthritis, and other lymphoproliferative disorders. The diagnosis is sometimes suggested by flow cytometry demonstrating an increased number of CD8+ CD57+ T cells and in a proportion of cases, this is confirmed by T-cell receptor gene rearrangement studies. Alternatively, T-LGL may be diagnosed on a bone marrow trephine, sometimes as an unsuspected, incidental finding. In a trephine, there may be a qualitative increase in the numbers of T-cells, sometimes with cluster formation and usually with an inversion of the CD4+:CD8+ T-cell ratio, although this finding is not specific to T-LGL.

PCR-based T-cell receptor gene rearrangement studies may fail (a common problem on bone marrow trephines) or give results that are monoclonal, oligoclonal or polyclonal, which show incomplete correlation with clinical diagnosis, viz T-LGL is often monoclonal, but strong immune responses to the lymphoma or to other conditions in the bone marrow or lymph node, such as the presence of another neoplasm, e.g., a B-cell lymphoma, myeloma or a myelodysplastic syndrome may make monoclonal results harder to document. Similarly, the presence of only a small number of T-cells can result in a monoclonal result, known as pseudo-clonality. T-cell gene rearrangement studies undertaken on peripheral blood are subject to similar limitations. Therefore, in a significant proportion of cases in which T-LGL may be present, no conclusive diagnosis can be reached and an expectant "watch and wait" approach is taken.

As described with reference to skin lymphomas, TRBC1/2 analysis by techniques of the present invention, such as (but not limited to) histology can be specifically applied to a population of cells defined on the basis of their morphological appearance, immunophenotype (e.g., larger size, expression of CD4 or CD8 or CD30) or other characteristics to determine whether there is skewing towards TRBC1 or TRBC2. If, for example, 90% (or 80% or 70% or 60%) of the CD8+ T-cells are TRBC1-restricted (i.e., express TRBC1 not TRBC2), then one can conclude that this is T-LGL and treat the patient with chemotherapeutic agents such as steroids, methotrexate, cyclophosphamide. The sooner this can be instigated, the better the prognosis. As discussed earlier, the TRBC1/2 analysis of the present invention can be undertaken cheaply and quickly, in less than 24 hours, providing a more reliable, conclusive and rapid result.

The methods of the invention used to analyse TRBC1/2 expression levels allow more accurate diagnosis of the presence or absence of lymphoma in a bone marrow or lymph node or other tissue or blood sample. This is of critical importance in determining whether a skin lymphoma, for example, is treated by local radiotherapy to the skin, or by systemic chemotherapy.

Furthermore, some systemic T-cell lymphomas can present initially with relatively low levels of involvement of bone marrow (e.g., the lymphoma contributes 20-30% of the cells in the marrow) and diagnosis is inconclusive even after morphological and immunohistochemical examination and PCR-based T-cell receptor gene rearrangement studies. Radiological examination and peripheral blood analysis may be attempted, to try and reach diagnosis, but are often inconclusive. One then adopts an expectant ("watch and wait") approach, until either a second trephine or lymph node biopsy shows a much higher level of involvement by lymphoma that allows conclusive diagnosis on morphological and immunohistochemical examination or one waits for a mass to develop somewhere that can be identified radiologically and biopsied to yield a definitive histological diagnosis. It should be noted that a proportion of patients die due to the inability to reach a diagnosis and consequent delay in treatment. As for T-LGL above, application of TRBC1/2 analysis by techniques such as (but not limited to) histology could lead to rapid diagnosis on the initial bone marrow trephine, leading to a much more rapid instigation of treatment and better patient outcome.

4. T-Cell Lymphomas in Lymph Nodes

While some T-cell lymphomas are composed of overtly neoplastic-looking cells when viewed under the microscope. In a lymph node, they frequently grow in the paracortex, the part of the lymph node that usually contains abundant T-cells. It can then be very difficult to determine whether or not a lymphoma is present and expensive and time-consuming PCR-based clonality studies are undertaken, which often fail to give a conclusive result, as there are also many non-neoplastic cells in the lymph node that may obscure the clonal nature of the PCR study.

TRBC1/2 analysis as described in the present invention would solve this problem. For example, by using oligonucleotides or antibodies according to the invention TRBC1/2 analysis can be applied to a population of cells which may also be defined on the basis of their morphological appearance, immunophenotype (e.g., larger size, expression of CD4 or CD8 or CD30) or other characteristics. If, for example, 90% (or 80% or 70% or 60%) of the CD4+ T-cells are TRBC1-restricted (i.e., express TRBC1 not TRBC2), then one may be able to conclude that this is lymphoma rather than a benign population of T-cells and treat the patient with radiotherapy, chemotherapy or other appropriate treatments. It should also be noted that such TRBC1/2 analysis according to the invention may be undertaken cheaply and quickly, in less than 24 hours, while T-cell receptor gene rearrangement studies will take one to several weeks. The present invention provides a more reliable, conclusive and rapid result that can be obtained more cheaply.

Sequence IDs
SEQ ID NO: 1 TRBC1 mRNA 3' untranslated region, shown in FIG. 1, the end of the last exon is shown in bold and the main 3' polyadenylation site is shown underlined-
GTCAAGAGAAAGGATTTCTGAAGGCAGCCCTGGAAGTGGAGTTAGGAGCT

TCTAACCCGTCATGGTTTCAATACACATTCTTCTTTTGCCAGCGCTTCTG

AAGAGCTGCTCTCACCTCTCTGCATCCCAATAGATATCCCCCTATGTGCA

TGCACACCTGCACACTCACGGCTGAAATCTCCCTAACCCAGGGGGACCTT

AGCATGCCTAAGTGACTAAACCAATAAA

SEQ ID NO: 2 TRBC2 mRNA 3' untranslated region, shown in FIG. 1, the end of the last exon is shown in bold and the main 3' polyadenylation site is shown underlined-
GTCAAGAGAAAGGATTCCAGAGGCTAGCTCCAAAACCATCCCAGGTCATT

CTTCATCCTCACCCAGGATTCTCCTGTACCTGCTCCCAATCTGTGTTCCT

AAAAGTGATTCTCACTCTGCTTCTCATCTCCTACTTACATGAATACTTCT

CTCTTTTTTCTGTTTCCCTGAAGATTGAGCTCCCAACCCCCAAGTACGAA

ATAGGCTAAACCAATAAA

SEQ ID NO: 3 TRBC1 exons and 3'UTR shown in FIG. 7.

SEQ ID NO: 4 TRBC2 exons and 3'UTR shown in FIG. 7.

SEQ ID NO: 5 TRBC1 protein sequence shown in FIG. 6.

SEQ ID NO: 6 TRBC2 protein sequence shown in FIG. 6.

SEQ ID NO: 7 TRGC1 protein sequence shown in FIG. 5-
XKQLDADVSPKPTIFLPSIAETKLQKAGTYLCLLEKFFPDVIKIHWQEKK

SNTILGSQEGNTMKTNDTYMKFSWLTVPEKSLDKEHRCIVRHENNKNGVD

QEIIFPPIKTDVITMDPKDNCSKDANDTLLLQLTNTSAYYMYLLLLLKSV

VYFAIITCCLLRRTAFCCNGEKS

SEQ ID NO: 8 TRGC2 protein sequence shown in FIG. 5-
XKQLDADVSPKPTIFLPSIAETKLQKAGTYLCLLEKFFPDIIKIHWQEKK

SNTILGSQEGNTMKTNDTYMKFSWLTVPEESLDKEHRCIVRHENNKNGID

QEIIFPPIKTDVTTVDPKYNYSKDANDVITMDPKDNWSKDANDTLLLQLT

NTSAYYTYLLLLLKSVVYFAIITCCLLRRTAFCCNGEKS

SEQ ID NO: 9 TRBC1 Cβ1 primer forward:
ACCCTGTATGCTGTGCTGGT,
shown in FIG. 2.

SEQ ID NO: 10 TRBC1 Cβ1 primer reverse:
GGGATGCAGAGAGGTGAGAG,
shown in FIG. 2.

SEQ ID NO: 11 TRBC2 Cβ2 primer forward:
ACCTTGTATGCCGTGCTGGT,
shown in FIG. 2.

SEQ ID NO: 12 TRBC2 Cβ2 primer Reverse:
CTGGGATGGTTTTGGAGCTA,
shown in FIG. 2.

SEQ ID NO: 13 TRGC1 exons and 3'UTR shown in FIG. 8.

SEQ ID NO: 14 TRGC2 exons and 3'UTR shown in FIG. 8.

SEQ ID NO: 15-
CCATGTCAAGAGAAAGGATTTCTGAAGGCAGCCCTGGAAGTGGAGTTAGG

AGCTTCTAACCCGTCATGGTTTCAATACACATTCTTCTTTTGCCAGCGCT

TCTGAAGAGCTGCTCTCACCTCTCTGCATCCCAATAGATATCCCCCTATG

TGCATGCACACCTGCACACTCACGGCTGAAATCTCCCTAACCCAGGGGGA

CCTTAGCATGCCTAAGTGACTAAACC

SEQ ID NO: 16-
CATGGTGTCAAGAGAAAGGATTCCAGAGGCTAGCTCCAAAACCATCCCAG

GTCATTCTTCATCCTCACCCAGGATTCTCCTGTACCTGCTCCCAATCTGT

GTTCCTAAAAGTGATTCTCACTCTGCTTCTCATCTCCTACTTACATGAAT

ACTTCTCTCTTTTTTCTGTTTCCCTGAAGATTGAGCTCCCAACCCCCAAG

TACGAAATAGGCTAAACC

SEQ ID NO: 17-
ACCATGACGGGTTAGAAGCT

SEQ ID NO: 18-
TTAGGGAGATTTCAGCCGTGA

SEQ ID NO: 19-
TGGGTTAGGGAGATTTCAGCC

SEQ ID NO: 20-
ATTGGGATGCAGAGAGGTGAG

SEQ ID NO: 21-
TGTGTATTGAAACCATGACGG

SEQ ID NO: 22-
CTAACTCCACTTCCAGGGCTG

SEQ ID NO: 23-
TGTAAGTAGGAGATGAGAAGCA

SEQ ID NO: 24-
TTGGGAGCAGGTACAGGAGAAT

SEQ ID NO: 25-
AGGATGAAGAATGACCTGGGAT

SEQ ID NO: 26-
GCCTATTTCGTACTTGGGGGT

SEQ ID NO: 27-
GTAAGTAGGAGATGAGAAGCAG

SEQ ID NO: 28-
AGGAACACAGATTGGGAGCAG

SEQ ID NO: 29-
CCTGGGATGGTTTTGGAGCTA

SEQ ID NO: 30- Actin primer forward:
GGACTTCGAGCAAGAGATGG

SEQ ID NO: 31- Actin primer reverse:
AGCACTGTGTTGGCGTACAG

SEQ ID NO: 32- Reversed and complemented TRBC2 target sequence shown in FIG. 17:
TTTATTGGTTTAGCCTATTTCGTACTTGGGGGTTGGGAGCTCAATCTTCA

GGGAAACAGAAAAAAGAGAGAAGTATTCATGTAAGTAGGAGATGAGAAGC

AGAGTGAGAATCACTTTTAGGAACACAGATTGGGAGCAGGTACAGGAGAA

TCCTGGGTGAGGATGAAGAATGACCTGGGATGGTTTTGGAGCTAGCCTCT

GGAATCCTTTCTCTTGAC

SEQ ID NO: 33- Reversed and complemented TRBC1 target sequence shown in FIG. 18:
TTTATTGGTTTAGTCACTTAGGCATGCTAAGGTCCCCCTGGGTTAGGGAG

ATTTCAGCCGTGAGTGTGCAGGTGTGCATGCACATAGGGGGATATCTATT

GGGATGCAGAGAGGTGAGAGCAGCTCTTCAGAAGCGCTGGCAAAAGAAGA

ATGTGTATTGAAACCATGACGGGTTAGAAGCTCCTAACTCCACTTCCAGG

GCTGCCTTCAGAAATCCTTTCTCTTGAC

The invention claimed is:

1. A method of determining a percentage of T cells which express TRBC1 and a percentage of T cells which express TRBC2, comprising:
   (a) obtaining a solid or liquid tissue sample or a cell sample from a subject, wherein the subject and/or the sample are suspected of having neoplastic T-cell;
   (b) contacting the solid or liquid tissue sample or the cell sample with one or more detection reagents that recognize the 3' untranslated region of TRBC1 and one or more detection reagents that recognize the 3' untranslated region of TRBC2;
   (c) detecting expression of the 3' untranslated region of TRBC1 by the one or more detection reagents that recognize the 3' untranslated region of TRBC1 and detecting expression of the 3' untranslated region of TRBC2 by the one or more detection reagents that recognize the 3' untranslated region of TRBC2, thereby determining the percentage of T cells that express TRBC1 and the percentage of T cells that express TRBC2,
   (d) identifying the sample as neoplastic when more than 60%, 70%, 80%, 85%, 90% of the T-cells express TRBC1 or when more than 60%, 70%, 80%, 85%, 90% of the T-cells express TRBC2, and
   (e) treating the subject identified in step d with a radiotherapy or chemotherapy.

2. The method according to claim 1 wherein the one or more detection reagents is an oligonucleotide probe, a pair of oligonucleotides or a set of oligonucleotides wherein at least one of the oligonucleotides binds to a region that is different between TRBC1 and TRBC2.

3. The method according to claim 1 wherein the one or more detection reagents are labelled either directly or indirectly with a detectable label.

* * * * *

SEQUENCE LISTING

<160> NUMBER OF SEQ ID NOS: 33

<210> SEQ ID NO 1
<211> LENGTH: 228
<212> TYPE: DNA
<213> ORGANISM: Homo sapiens

<400> SEQUENCE: 1

| | | | | | |
|---|---|---|---|---|---|
| gtcaagagaa | aggatttctg | aaggcagccc | tggaagtgga | gttaggagct | tctaacccgt | 60 |
| catggtttca | atacacattc | ttcttttgcc | agcgcttctg | aagagctgct | ctcacctctc | 120 |
| tgcatcccaa | tagatatccc | cctatgtgca | tgcacacctg | cacactcacg | gctgaaatct | 180 |
| ccctaaccca | ggggaccctt | agcatgccta | agtgactaaa | ccaataaa | | 228 |

<210> SEQ ID NO 2
<211> LENGTH: 218
<212> TYPE: DNA
<213> ORGANISM: Homo sapiens

<400> SEQUENCE: 2

| | | | | | |
|---|---|---|---|---|---|
| gtcaagagaa | aggattccag | aggctagctc | caaaaccatc | ccaggtcatt | cttcatcctc | 60 |
| acccaggatt | ctcctgtacc | tgctcccaat | ctgtgttcct | aaaagtgatt | ctcactctgc | 120 |
| ttctcatctc | ctacttacat | gaatacttct | ctcttttttc | tgtttccctg | aagattgagc | 180 |
| tcccaacccc | caagtacgaa | ataggctaaa | ccaataaa | | | 218 |

<210> SEQ ID NO 3
<211> LENGTH: 915
<212> TYPE: DNA
<213> ORGANISM: Homo sapiens

<400> SEQUENCE: 3

| | | | | | |
|---|---|---|---|---|---|
| aggacctgaa | caaggtgttc | ccacccgagg | tcgctgtgtt | tgagccatca | gaagcagaga | 60 |
| tctcccacac | ccaaaaggcc | acactggtgt | gcctggccac | aggcttcttc | cccgaccacg | 120 |
| tggagctgag | ctggtgggtg | aatgggaagg | aggtgcacag | tggggtcagc | acggaccgc | 180 |
| agcccctcaa | ggagcagccc | gccctcaatg | actccagata | ctgcctgagc | agccgcctga | 240 |
| gggtctcggc | caccttctgg | cagaaccccc | gcaaccactt | ccgctgtcaa | gtccagttct | 300 |
| acgggctctc | ggagaatgac | gagtggaccc | aggatagggc | caaacccgtc | acccagatcg | 360 |
| tcagcgccga | ggcctggggt | agagcagact | gtggctttac | ctcggtgtcc | taccagcaag | 420 |
| gggtcctgtc | tgccaccatc | ctctatgaga | tcctgctagg | gaaggccacc | ctgtatgctg | 480 |
| tgctggtcag | cgcccttgtg | ttgatggcca | tggtcaagag | aaaggatttc | tgaaggcagc | 540 |
| cctggaagtg | gagttaggag | cttctaaccc | gtcatggttt | caatacacat | tcttcttttg | 600 |
| ccagcgcttc | tgaagagctg | ctctcacctc | tctgcatccc | aatagatatc | cccctatgtg | 660 |
| catgcacacc | tgcacactca | cggctgaaat | ctccctaacc | caggggacc | ttagcatgcc | 720 |
| taagtgacta | aaccaataaa | aatgtttctgg | tctggcctga | ctctgacttg | tgaatgtctg | 780 |
| gatagctcct | tggctgtctc | tgaactccct | gtgactctcc | ccattcagtc | aggatagaaa | 840 |
| caagaggtat | tcaaggaaaa | tgcagactct | tcacgtaaga | gggatgaggg | gcccaccttg | 900 |
| agatcaatag | cagaa | | | | | 915 |

<210> SEQ ID NO 4
<211> LENGTH: 905
<212> TYPE: DNA
<213> ORGANISM: Homo sapiens

<400> SEQUENCE: 4

```
aggacctgaa aaacgtgttc ccacccgagg tcgctgtgtt tgagccatca gaagcagaga      60
tctcccacac ccaaaaggcc acactggtgt gcctggccac aggcttctac cccgaccacg     120
tggagctgag ctggtgggtg aatgggaagg aggtgcacag tggggtcagc acagaccccgc   180
agccccctcaa ggagcagccc gccctcaatg actccagata ctgcctgagc agccgcctga    240
gggtctcggc caccttctgg cagaaccccc gcaaccactt ccgctgtcaa gtccagttct     300
acgggctctc ggagaatgac gagtggaccc aggataggc caaacctgtc acccagatcg      360
tcagcgccga ggcctggggt agagcagact gtggcttcac ctccgagtct taccagcaag    420
gggtcctgtc tgccaccatc ctctatgaga tcttgctagg aaggccacc ttgtatgccg      480
tgctggtcag tgccctcgtg ctgatggcca tggtcaagag aaaggattcc agaggctagc    540
tccaaaacca tcccaggtca ttcttcatcc tcacccagga ttctcctgta cctgctccca    600
atctgtgttc ctaaaagtga ttctcactct gcttctcatc tcctacttac atgaatactt    660
ctctcttttt tctgtttccc tgaagattga gctcccaacc cccaagtacg aaataggcta    720
aaccaataaa aaattgtgtg ttgggcctgg ttgcatttca ggagtgtctg tggagttctg    780
ctcatcactg acctatcttc tgatttaggg aaagcagcat tcgcttggac atctgaagtg    840
acagccctct ttctctccac ccaatgctgc tttctcctgt tcatcctgat ggaagtctca    900
acaca                                                                905
```

<210> SEQ ID NO 5
<211> LENGTH: 176
<212> TYPE: PRT
<213> ORGANISM: Homo sapiens

<400> SEQUENCE: 5

```
Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175
```

<210> SEQ ID NO 6
<211> LENGTH: 178

<212> TYPE: PRT
<213> ORGANISM: Homo sapiens

<400> SEQUENCE: 6

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 7
<211> LENGTH: 173
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 7

Xaa Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Val Ile Lys Ile His Trp Gln Glu
        35                  40                  45

Lys Lys Ser Asn Thr Ile Leu Gly Ser Gln Gly Asn Thr Met Lys
    50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
130                 135                 140

```
Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
            165                 170
```

<210> SEQ ID NO 8
<211> LENGTH: 189
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 8

```
Xaa Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Ile Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Glu
65                  70                  75                  80

Ser Leu Asp Lys Glu His Arg Cys Ile Val Arg His Glu Asn Asn Lys
                85                  90                  95

Asn Gly Ile Asp Gln Glu Ile Ile Phe Pro Pro Ile Lys Thr Asp Val
            100                 105                 110

Thr Thr Val Asp Pro Lys Tyr Asn Tyr Ser Lys Asp Ala Asn Asp Val
        115                 120                 125

Ile Thr Met Asp Pro Lys Asp Asn Trp Ser Lys Asp Ala Asn Asp Thr
    130                 135                 140

Leu Leu Leu Gln Leu Thr Asn Thr Ser Ala Tyr Tyr Thr Tyr Leu Leu
145                 150                 155                 160

Leu Leu Leu Lys Ser Val Val Tyr Phe Ala Ile Ile Thr Cys Cys Leu
                165                 170                 175

Leu Arg Arg Thr Ala Phe Cys Cys Asn Gly Glu Lys Ser
            180                 185
```

<210> SEQ ID NO 9
<211> LENGTH: 20
<212> TYPE: DNA
<213> ORGANISM: Homo sapiens

<400> SEQUENCE: 9
accctgtatg ctgtgctggt          20

<210> SEQ ID NO 10
<211> LENGTH: 20
<212> TYPE: DNA
<213> ORGANISM: Homo sapiens

<400> SEQUENCE: 10
gggatgcaga gaggtgagag          20

<210> SEQ ID NO 11
<211> LENGTH: 20
<212> TYPE: DNA
<213> ORGANISM: Homo sapiens

<400> SEQUENCE: 11
accttgtatg ccgtgctggt                                              20

<210> SEQ ID NO 12
<211> LENGTH: 20
<212> TYPE: DNA
<213> ORGANISM: Homo sapiens

<400> SEQUENCE: 12
ctgggatggt tttggagcta                                              20

<210> SEQ ID NO 13
<211> LENGTH: 958
<212> TYPE: DNA
<213> ORGANISM: Homo sapiens

<400> SEQUENCE: 13
gataaacaac ttgatgcaga tgtttccccc aagcccacta ttttcttcc ttcaattgct    60
gaaacaaagc tccagaaggc tggaacatac ctttgtcttc ttgagaaatt tttccctgat   120
gttattaaga tacattggga agaaaagaag agcaacacga ttctgggatc ccaggagggg   180
aacaccatga agactaatga cacatacatg aaatttagct ggttaacggt gccagaaaag   240
tcactggaca agaacacag atgtatcgtc agacatgaga ataataaaaa cggagttgat    300
caagaaatta tctttcctcc aataaagaca gatgtcatca caatggatcc caagacaat    360
tgttcaaaag atgcaaatga tacactactg ctgcagctca caaacacctc tgcatattac   420
acgtacctcc tcctgctcct caagagtgtg gtctatttg ccatcatcac ctgctgtctg     480
cttagaagaa cggctttctg ctgcaatgga gagaaatcat aacagacggt ggcacaagga   540
ggccatcttt tcctcatcgg ttattgtccc tagaagcgtc ttctgaggat ctagttgggc   600
tttctttctg ggtttgggcc atttcagttc ttatgtgtgt actattctat ctattgtata   660
acggttttca aaccagtggg cacacagaga acctcactct gtaataacaa tgaggaatag   720
ccacggcgat ctccagcacc aatctctcca tgttttccac agctcctcca gccaacccaa   780
atagcgcctg ctatagtgta gacatcctgc ggcttctagc cttgtccctc tcttagtgtt   840
ctttaatcag ataactgcct ggaagccttt cattttacac gccctgaagc agtcttcttt   900
gctagttgaa ttatgtggtg tgtttttccg taataagcaa aataaattta aaaaatg      958

<210> SEQ ID NO 14
<211> LENGTH: 1013
<212> TYPE: DNA
<213> ORGANISM: Homo sapiens

<400> SEQUENCE: 14
gataaacaac ttgatgcaga tgtttccccc aagcccacta ttttcttcc ttcaattgct    60
gaaacaaaac tccagaaggc tggaacatac ctttgtcttc ttgagaaatt tttcccagat   120
attattaaga tacattggca agaaaagaag agcaacacga ttctgggatc ccaggagggg   180
aacaccatga agactaacga cacatacatg aaatttagct ggttaacggt gccagaagag   240
tcactggaca agaacacag atgtatcgtc agacatgaga ataataaaaa cggaattgat    300
caagaaatta tctttcctcc aataaagaca gatgtcacca cagtggatcc caaatacaat   360
tattcaaagg atgcaaatga tgtcatcaca atggatccca agacaattg gtcaaaagat    420
gcaaatgata cactactgct gcagctcaca aacacctctg catattacat gtacctcctc   480

| | |
|---|---|
| ctgctcctca agagtgtggt ctattttgcc atcatcacct gctgtctgct tggaagaacg | 540 |
| gctttctgct gcaatggaga gaaatcataa cagacggtgg cacaaggagg ccatcttttc | 600 |
| ctcatcggtt attgtccctca gaagcgtctt ctgaggatct agttgggctt tctttctggg | 660 |
| tttgggccat ttcagttctc atgtgtgtac tattctatct attgtataat ggttttcaaa | 720 |
| ccagtgggca cacagagaac ctcactctgt aataacaatg aggaatagcc atggcgatct | 780 |
| ccagcaccaa tctctccatg ttttccacag ctcctccagc caacccaaat agcgcctgct | 840 |
| atagtgtaga cagcctgcgg cttctagcct tgtccctctc ttagtgttct ttaatcagat | 900 |
| aactgcctgg aagcctttca ttttacacgc cctgaagcag tcttctttgc tagttgaatt | 960 |
| atgtggtgtg ttttccgta ataagcaaaa taaatttaaa aaaatgaaaa gtt | 1013 |

<210> SEQ ID NO 15
<211> LENGTH: 226
<212> TYPE: DNA
<213> ORGANISM: Homo sapiens

<400> SEQUENCE: 15

| | |
|---|---|
| ccatgtcaag agaaaggatt tctgaaggca gccctggaag tggagttagg agcttctaac | 60 |
| ccgtcatggt ttcaatacac attcttcttt tgccagcgct tctgaagagc tgctctcacc | 120 |
| tctctgcatc ccaatagata tcccctatg tgcatgcaca cctgcacact cacggctgaa | 180 |
| atctccctaa cccagggga ccttagcatg cctaagtgac taaacc | 226 |

<210> SEQ ID NO 16
<211> LENGTH: 218
<212> TYPE: DNA
<213> ORGANISM: Homo sapiens

<400> SEQUENCE: 16

| | |
|---|---|
| catggtgtca agagaaagga ttccagaggc tagctccaaa accatcccag gtcattcttc | 60 |
| atcctcaccc aggattctcc tgtacctgct cccaatctgt gttcctaaaa gtgattctca | 120 |
| ctctgcttct catctcctac ttacatgaat acttctctct ttttctgtt tccctgaaga | 180 |
| ttgagctccc aaccccaag tacgaaatag gctaaacc | 218 |

<210> SEQ ID NO 17
<211> LENGTH: 20
<212> TYPE: DNA
<213> ORGANISM: Homo sapiens

<400> SEQUENCE: 17

| | |
|---|---|
| accatgacgg gttagaagct | 20 |

<210> SEQ ID NO 18
<211> LENGTH: 21
<212> TYPE: DNA
<213> ORGANISM: Homo sapiens

<400> SEQUENCE: 18

| | |
|---|---|
| ttagggagat ttcagccgtg a | 21 |

<210> SEQ ID NO 19
<211> LENGTH: 21
<212> TYPE: DNA
<213> ORGANISM: Homo sapiens

<400> SEQUENCE: 19

| | |
|---|---|
| tgggttaggg agatttcagc c | 21 |

<210> SEQ ID NO 20
<211> LENGTH: 21
<212> TYPE: DNA
<213> ORGANISM: Homo sapiens

<400> SEQUENCE: 20
attgggatgc agagaggtga g                                     21

<210> SEQ ID NO 21
<211> LENGTH: 21
<212> TYPE: DNA
<213> ORGANISM: Homo sapiens

<400> SEQUENCE: 21
tgtgtattga aaccatgacg g                                     21

<210> SEQ ID NO 22
<211> LENGTH: 21
<212> TYPE: DNA
<213> ORGANISM: Homo sapiens

<400> SEQUENCE: 22
ctaactccac ttccagggct g                                     21

<210> SEQ ID NO 23
<211> LENGTH: 22
<212> TYPE: DNA
<213> ORGANISM: Homo sapiens

<400> SEQUENCE: 23
tgtaagtagg agatgagaag ca                                    22

<210> SEQ ID NO 24
<211> LENGTH: 22
<212> TYPE: DNA
<213> ORGANISM: Homo sapiens

<400> SEQUENCE: 24
ttgggagcag gtacaggaga at                                    22

<210> SEQ ID NO 25
<211> LENGTH: 22
<212> TYPE: DNA
<213> ORGANISM: Homo sapiens

<400> SEQUENCE: 25
aggatgaaga atgacctggg at                                    22

<210> SEQ ID NO 26
<211> LENGTH: 21
<212> TYPE: DNA
<213> ORGANISM: Homo sapiens

<400> SEQUENCE: 26
gcctatttcg tacttgsgggg t                                    21

<210> SEQ ID NO 27
<211> LENGTH: 22
<212> TYPE: DNA
<213> ORGANISM: Homo sapiens

<400> SEQUENCE: 27

```
gtaagtagga gatgagaagc ag                                              22
```

```
<210> SEQ ID NO 28
<211> LENGTH: 21
<212> TYPE: DNA
<213> ORGANISM: Homo sapiens

<400> SEQUENCE: 28
aggaacacag attgggagca g                                               21

<210> SEQ ID NO 29
<211> LENGTH: 21
<212> TYPE: DNA
<213> ORGANISM: Homo sapiens

<400> SEQUENCE: 29
cctgggatgg ttttggagct a                                               21

<210> SEQ ID NO 30
<211> LENGTH: 20
<212> TYPE: DNA
<213> ORGANISM: Homo sapiens

<400> SEQUENCE: 30
ggacttcgag caagagatgg                                                 20

<210> SEQ ID NO 31
<211> LENGTH: 20
<212> TYPE: DNA
<213> ORGANISM: Homo sapiens

<400> SEQUENCE: 31
agcactgtgt tggcgtacag                                                 20

<210> SEQ ID NO 32
<211> LENGTH: 218
<212> TYPE: DNA
<213> ORGANISM: Homo sapiens

<400> SEQUENCE: 32
tttattggtt tagcctattt cgtacttggg ggttgggagc tcaatcttca gggaaacaga     60
aaaaagagag aagtattcat gtaagtagga gatgagaagc agagtgagaa tcacttttag   120
gaacacagat tgggagcagg tacaggagaa tcctgggtga ggatgaagaa tgacctggga   180
tggttttgga gctagcctct ggaatccttt ctcttgac                           218

<210> SEQ ID NO 33
<211> LENGTH: 228
<212> TYPE: DNA
<213> ORGANISM: Homo sapiens

<400> SEQUENCE: 33
tttattggtt tagtcactta ggcatgctaa ggtcccctg ggttagggag atttcagccg      60
tgagtgtgca ggtgtgcatg catataggg gatatctatt gggatgcaga gaggtgagag    120
cagctcttca gaagcgctgg caaaagaaga atgtgtattg aaaccatgac gggttagaag   180
ctcctaactc cacttccagg gctgccttca gaaatccttt ctcttgac                228
```